United States Patent
Feikert et al.

(10) Patent No.: US 10,106,859 B2
(45) Date of Patent: Oct. 23, 2018

(54) METHODS FOR IDENTIFYING PLANTS WITH EXTENDED SHELF LIFE

(71) Applicant: SEMINIS VEGETABLE SEEDS, INC., St. Louis, MO (US)

(72) Inventors: Michele Feikert, St. Louis, MO (US); Byron Froman, Davis, CA (US); Graeme S. Garvey, St. Louis, MO (US); Leo Kelly, St. Louis, MO (US); William Waycott, San Luis Obispo, CA (US)

(73) Assignee: Seminis Vegetable Seeds, Inc., Woodland, CA (US)

( * ) Notice: Subject to any disclaimer, the term of this patent is extended or adjusted under 35 U.S.C. 154(b) by 0 days.

(21) Appl. No.: 15/343,061

(22) Filed: Nov. 3, 2016

(65) Prior Publication Data

US 2017/0114418 A1 Apr. 27, 2017

Related U.S. Application Data

(62) Division of application No. 14/035,756, filed on Sep. 24, 2013, now Pat. No. 9,506,076.

(60) Provisional application No. 61/704,602, filed on Sep. 24, 2012.

(51) Int. Cl.
*C12Q 1/68* (2018.01)
*C12Q 1/6895* (2018.01)

(52) U.S. Cl.
CPC .................. *C12Q 1/6895* (2013.01)

(58) Field of Classification Search
None
See application file for complete search history.

(56) References Cited

U.S. PATENT DOCUMENTS

| | | | |
|---|---|---|---|
| 6,242,221 | B1 | 6/2001 | Robinson |
| 7,122,719 | B2 | 10/2006 | Hakimi |
| 7,381,810 | B2 | 6/2008 | Robinson |
| 7,777,101 | B2 | 8/2010 | Van Dun et al. |
| 8,563,805 | B2 * | 10/2013 | Armstrong ........... C12N 9/0059 435/320.1 |
| 8,642,505 | B2 | 2/2014 | Kohn |
| 9,121,022 | B2 | 9/2015 | Sammons et al. |
| 2015/0247153 | A1 | 9/2015 | Fillatti et al. |

FOREIGN PATENT DOCUMENTS

| | | |
|---|---|---|
| EP | 2 055 782 B1 | 8/2010 |
| WO | WO 94/03607 | 2/1994 |
| WO | WO 2007/077229 | 7/2007 |
| WO | WO 2012/125025 | 9/2012 |

OTHER PUBLICATIONS

Richter et al, 2012, MPMI, 25:200-210.*
Tran et al, 2012, BMC Genomics, 13:1-12.*
Fang et al, 2010, PLoS Computational Biology, 6:1-8.*
Chery, "RNA therapeutics: RNAi and antisense mechanisms and clinical applications," *Postdoc Journal* 4:35-50, 2016.
Watts, et al., "Gene silencing by siRNAs and antisense oligonucleotides in the laboratory and the clinic," *The Journal of Pathology* 226:365-379, 2012.
Atkinson et al., "An intra-specific linkage map of lettuce (*Lactuca sativa*) and genetic analysis of postharvest discolouration traits," *Theor. Appl. Genet.* 126(11):2737-2752, Nov. 2013.
Atkinson et al., "A study of variation in the tendency for postharvest discoloration in a lettuce (*Lactuca sativa*) diversity set," *International Journal of Food Science & Technology* 48(4):801-807, Apr. 2013.
GenBank Accession No. JI578945.1, dated Apr. 11, 2011.
GenBank Accession No. BQ867950.1, dated Jan. 2, 2011.
GenBank Accession No. JN001935.1, dated Oct. 20, 2011.
Martinez et al., "The biochemistry and control of enzymatic browning," *Trends in Food Science & Technology* 6(6):195-200, Jun. 1995.
Richter et al."Silencing and Heterologous Expression of ppo-2 Indicate a Specific Function of a Single Polyphenol Oxidase Isoform in Resistance of Dandelion(*Taraxacum officinale*) Against *Pseudonmonas syringae* pv. Tomato,", MPMI, 25:200-210: 2012.
Solano et al., "Isolation and Characterization of Strain MMB-1 (CECT 4803), a Novel Melanogenic Marine Bacterium," *Appl. Environ. Microbiol.* 63(9):3499, 1997.
Tran et al, "The polyphenol oxidase gene family in land plants: Lineage-specific duplication and expansion," BMS Genomics, 13:1-12; 2012.
Sequence No. 1 Pair Wise Alignments; 2016.
Momentive Performance Materials Inc. Marketing Bulleting for Silwet L-77* Ag spray adjuvant DA Performance Additives, 1-4; 2011.
European Extended Search Report regarding European Application No. EP13838210, dated Mar. 31, 2016.
International Search Report and Written Opinion issued in PCT/US13/61475, dated Apr. 8, 2014.
New Zealand Office Action regarding Application No. 630577, dated Dec. 16, 2015.

* cited by examiner

*Primary Examiner* — Jason Deveau Rosen
(74) *Attorney, Agent, or Firm* — Alissa Eagle, Esq.; Dentons US LLP

(57) ABSTRACT

The invention provides compositions and methods related to selective inhibition of PPO11 and use for improving shelf life of a plant or parts thereof. In accordance with the invention, for example, compositions for topical application to a plant or part thereof, are provided that can reduce browning of the plant or part thereof to extend shelf life.

9 Claims, 6 Drawing Sheets
Specification includes a Sequence Listing.

```
                        SEQUENCE LISTING

<160> NUMBER OF SEQ ID NOS: 32

<210> SEQ ID NO 1
<211> LENGTH: 189
<212> TYPE: DNA
<213> ORGANISM: Artificial sequence
<220> FEATURE:
<223> OTHER INFORMATION: Synthetic oligonucleotide

<400> SEQUENCE: 1
gataggagaa acgtcttatt aggtctcgga ggtctttacg gcgccgccgc cacttttggg      60
tcaaactcat tggcgtatgc agctccgatt atggcaccgg acctcacaaa atgtggtccg     120
gctgacttac cccaaggggc tgtacctaca aactgttgcc ctccatacac cacaaagatt     180
cacgatttc                                                             189

<210> SEQ ID NO 2
<211> LENGTH: 225
<212> TYPE: DNA
<213> ORGANISM: Artificial sequence
<220> FEATURE:
<223> OTHER INFORMATION: Synthetic oligonucleotide

<400> SEQUENCE: 2
gagaaaattt gtggcaaatt aatcgatgat ccaaatttcg caatcccttt ttggaactgg      60
gatgcacctg atggcatgaa gatccctgat atttacacga ataagaaatc tccgttgtac     120
gatgctcttc gtgatgcgaa gcatcaacca ccgtctctga ttgatcttga ctacaatggt     180
gacgatgaaa atcttagccg atcgaaacaa acctccacaa atctc                     225

<210> SEQ ID NO 3
<211> LENGTH: 225
<212> TYPE: DNA
<213> ORGANISM: Artificial sequence
<220> FEATURE:
<223> OTHER INFORMATION: Synthetic oligonucleotide

<400> SEQUENCE: 3
ggagatagga accagcaaaa tggtgaagac atgggtaact tttattctgc agccagagac      60
cctattttct atgcacatca tgcgaatatc gacagaatgt ggtcagtttg gaaaactcta     120
ggaggaagaa ggaatgattt tacagataaa gactggcttg attcttcgtt cttgttctac     180
gatgagaacg ctgaaatggt tcgagtcaag gtgagggatt gtctc                     225

<210> SEQ ID NO 4
<211> LENGTH: 226
<212> TYPE: DNA
<213> ORGANISM: Artificial sequence
<220> FEATURE:
<223> OTHER INFORMATION: Synthetic oligonucleotide

<400> SEQUENCE: 4
gagagatgag tttgcgaagt ttgatgtgtt tgtgaacgat gaagatgacg ggatgagggc      60
cacggctgat aagacggagt tcgccggaag ttttgttaat gtccctcata agcataagca     120
tgggaagaat gtgaagacaa gattgaggtt aggaataagt gagcttttgg aggatttggg     180
agctgaagat gatgacaacg tgttggtgac attggtgccg aaaaac                    226
```

<210> SEQ ID NO 5
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 5
atcgtcacca ttgtagtcaa gatca                                        25

<210> SEQ ID NO 6
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 6
atatcaggga tcttcatgcc atcag                                        25

<210> SEQ ID NO 7
<211> LENGTH: 25
<212> TYPE: RNA
<213> ORGANISM: Artificial sequence
<220> FEATURE:
<223> OTHER INFORMATION: Synthetic oligonucleotide

<400> SEQUENCE: 7
aucgucacca uuguagucaa gauca                                        25

<210> SEQ ID NO 8
<211> LENGTH: 25
<212> TYPE: RNA
<213> ORGANISM: Artificial sequence
<220> FEATURE:
<223> OTHER INFORMATION: Synthetic oligonucleotide

<400> SEQUENCE: 8
auaucaggga ucuucaugcc aucag                                        25

<210> SEQ ID NO 9
<211> LENGTH: 1922
<212> TYPE: DNA
<213> ORGANISM: Lactuca sativa

<400> SEQUENCE: 9
atggcatctc ttgcacaatc accaaccacc accaccacca ccggtggacg gtgcttctcc    60
tcctcctcca cgtactcttc ttccttctct ttcaaatcat ctcaagttcc catagcacga   120
atcacgaacc atcgccatgc agtttcatgc aaaggcgccc tagatgatga tgaccatcac   180
catgaaaact caggcaaatt tgataggaga aacgtcttat taggtctcgg aggtctttac   240
ggcgccgccg ccacttttgg gtcaaactca ttggcgtatg cagctccgat tatggcaccg   300
gacctcacaa aatgtggtcc ggctgactta ccccaagggg ctgtacctac aaactgttgc   360
cctccataca ccacaaagat tcacgatttc aaacttccac caccgtcaac caccttccga   420
gtccgtccgg cagctcattt ggctaataaa gattacatag ccaagttcaa taaagccatc   480
gagctcatga aagctctccc agatgacgat cctcgtagtt tcaagcaaca agctgctgtt   540
cattgtgcgt attgcgatgg ggcatacgat caagtcggtt ccctgatctc gagcttcaa   600 gtccatggct catggttgtt cttaccttc caccgctatt acttatactt cttcgagaaa   660
atttgtggca aattaatcga tgatccaaat ttcgcaatcc ctttttggaa ctgggatgca   720

```
cctgatggca tgaagatccc tgatatttac acgaataaga aatctccgtt gtacgatgct        780
cttcgtgatg cgaagcatca accaccgtct ctgattgatc ttgactacaa tggtgacgat        840
gaaaatctta gccgatcgaa acaaacctcc acaaatctca caattatgta cagacaaatg        900
gtgtctagtt ccaagactgc tagtcttttc atgggtagtc cttatcgtgc aggtgatgag        960
gctagccctg gctctggctc gctcgagagc ataccacatg gcccggttca tatctggacc       1020
ggagatagga accagcaaaa tggtgaagac atgggtaact tttattctgc agccagagac       1080
cctattttct atgcacatca tgcgaatatc gacagaatgt ggtcagtttg aaaaactcta       1140
ggaggaagaa ggaatgattt tacagataaa gactggcttg attcttcgtt cttgttctac       1200
gatgagaacg ctgaaatggt tcgagtcaag gtgagggatt gtctcgactc caagaagctt       1260
gggtacgttt atcaggatgt agagatacca tggctaaaaa gcaaacccga accacgtctg       1320
aaaagggctt tgagcaagat caagaagctc gctgtagctc gagccgatga acacataccc       1380
tttgcaaaag atgttttttcc ggcgagtctt gataaggtga taaaagtgct ggttccaagg       1440
ccgaagaaat caaggagcaa gaaacagaaa gaggatgaag aagaattttt ggtgatagaa       1500
ggaattgaac tgaagagaga tgagtttgcg aagtttgatg tgtttgtgaa cgatgaagat       1560
gacgggatga gggccacggc tgataagacg gagttcgccg gaagttttgt taatgtccct       1620
cataagcata agcatgggaa gaatgtgaag acaagattga ggttaggaat aagtgagctt       1680
ttggaggatt tgggagctga agatgatgac aacgtgttgg tgacattggt gccgaaaaac       1740
aaaggtggtg aagtttccat taaagggatt aaaatcgagc atgaggattg ataaaaataa       1800
cttttcattt tcttgaaaaa taaaaaacta tgattttgag ttgtttcggt aaatatgttg       1860
tcgcttggtt aatgtatcat caataaaaat aaatttcgaa atcaaagttg gatttgaacc       1920
cc                                                                      1922

<210> SEQ ID NO 10
<211> LENGTH: 1001
<212> TYPE: DNA
<213> ORGANISM: Artificial sequence
<220> FEATURE:
<223> OTHER INFORMATION: Synthetic oligonucleotide

<400> SEQUENCE: 10
aaaagtaaaa ataagttttt aaagtattcg tatttatatt ttaagaaata ttagtcaaat         60
ataatgaatt ttttttttatc caaattcaaa aaaacaaatg atatagtttt tcgtaatatt       120
attttaatga gttttttaaaa gaaatctttc aaaagtatta ttgttaagga tactcacatt       180
ttgtttaagt gattataagt ttttattaaa aaataaataa aacgtgaaaa ttttcgttct       240
ttaaatgaaa aaccttttta atggtttact aaatattata tattatgagc ttttttgaaat       300 ttaataaggt tatttagata caaaatttta ttttaaaaga ttacaagctt tgaaaataaa       360
aataaatatg atattattca aaatgattca aaatatttat gattaaaaaa attatgatta       420
aacatattta tgattttttaa ttgtttatga tctaaaaata tcataatcta aatattatga       480
tccttaatta cataatttat gattcaaaat taaatgtttt taatgatc taaaatttgt        540 tattaacaaa aaatttattt aagtgaatat attattatcc aaaattatat gattaaaata       600
tattataatc taaaatacta caattgattg tttaatgctc caaaattata tcatccaaaa       660
atagtaaata gtatgatatg aaaacataat gattcctaat atcttatgat tcaaaacgtt       720
tataaatttt aaacatcaaa acctcaaaca aatatttagt ttaaaaaaac aaaagaaaat       780
```

-continued

| | | |
|---|---|---|
| ctaaataata aaacaaaaac aaaaaacaca ataacttca aagatatact aaaatgctat | 840 | |
| atgaagtggt atgagtttct tacccgtgtg atgacatgga atgtaagtca tgcgtcagtt | 900 | |
| aggaggaaca atcagtggcg gagctagaag ttttcatttg gggcgccgaa aatagaattt | 960 | |
| gtataaaaat tgaagaacag aggggccaaa gtcaaacttt a | 1001 | |

<210> SEQ ID NO 11
<211> LENGTH: 1001
<212> TYPE: DNA
<213> ORGANISM: Lactuca sativa

<400> SEQUENCE: 11

| | | |
|---|---|---|
| aaaaccaaaa ttcacaaaat catttatcac attcgaatac aaaaactacc aacactaaat | 60 | |
| atttatattt aatttcaaag tatcgaaaat caaatgacat gttaaaagta tcaaaagtcg | 120 | |
| gtggcttggt aaaagtgtca atgtcttagg taggtgggtt gcttttttgg caaactttcc | 180 | |
| gtattttgtt atacatctta tcctttcttg tcttttggcc tcagtttctt tacaataaac | 240 | |
| tgcagatatg aaaacaaaag aataaacaaa ttacaaatgt caaacgctat aatattaata | 300 | |
| ataaggtaaa ttttttgaag tttgatgctt aaagaggaga aacgttggaa gtaaaacttg | 360 | |
| taatacagag aaatgaaagt tgttataaaa atgaaagtat gatgctataa tagaactata | 420 | |
| tttacaccaa gttcaaagta cgacactgta attagaaaaa ggtaaaaatg tacacaaaat | 480 | |
| aaacaaatgg aagtgcatca atcaaatcaa cttgagttct accttatgta cacatatcaa | 540 | |
| atgacagttt atggtgccaa tctacagcta attagcaccg gatgcacaag tgactaagaa | 600 | |
| aattttggta ttaatggttt taatcctatg tatgttgtaa gaaagattta tatgaaaaca | 660 | |
| tattgcattt tttaaaaggt agaaatatgt aacacccgga ttttcaacta ccgattaaat | 720 | |
| gacaaataat cgttccaaca tctcccatga tcaattctaa acttacgtat agactacact | 780 | |
| acaacggaag caaaattaaa taaaataaaa tcttcaattg aagaacttta ggtgttacat | 840 | |
| ctttacggaa ctcctttatc gtcttgttat acaatccctc tccttgcctt cttactgcca | 900 | |
| cttgctaaat agtttcctgg gttgcgcaca tataaagttt ctatatgggt aagcctaagg | 960 | |
| cctagtgagt tcgtgttgca catacatgtc catcagttaa c | 1001 | |

<210> SEQ ID NO 12
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 12
cgtcgagatt ctgcgagaaa g                                           21

<210> SEQ ID NO 13
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 13
gcaaacgtcg tcgatgtaag c                                           21

<210> SEQ ID NO 14
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 14
ctcctccgtg ttgttgatcg tgaatacgtc    30

<210> SEQ ID NO 15
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 15
gcaagttcaa taaagccatc ga    22

<210> SEQ ID NO 16
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 16
cgcaataggc acaatgaaca tt    22

<210> SEQ ID NO 17
<211> LENGTH: 29
<212> TYPE: DNA
<213> ORGANISM: Artificial sequence
<220> FEATURE:
<223> OTHER INFORMATION: Synthetic oligonucleotide

<400> SEQUENCE: 17
cccagatgac gatcctcgta gctttaagc    29

<210> SEQ ID NO 18
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 18
aaggcttcca gaaacatcaa gaa    23

<210> SEQ ID NO 19
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 19
agactcgccg gaaaaacatc t    21

<210> SEQ ID NO 20
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 20
catgcccatg aacacatacc ctttgca    27

-continued

<210> SEQ ID NO 21
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 21
gcaagatcaa gaagctcgct gta                                          23

<210> SEQ ID NO 22
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 22
actcgccgga aaacatctt t                                             21

<210> SEQ ID NO 23
<211> LENGTH: 26
<212> TYPE: DNA
<213> ORGANISM: Artificial sequence
<220> FEATURE:
<223> OTHER INFORMATION: Synthetic oligonucleotide

<400> SEQUENCE: 23
cgagccgatg aacacatacc ctttgc                                       26

<210> SEQ ID NO 24
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 24
gacgtaccat ggctaaaaag caa                                          23

<210> SEQ ID NO 25
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 25
cgatggattt cctcgcaact                                              20

<210> SEQ ID NO 26
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 26
ccagtcccac gtgcacccag g                                            21

<210> SEQ ID NO 27
<211> LENGTH: 19
<212> TYPE: DNA
<213> ORGANISM: Artificial sequence
<220> FEATURE:
<223> OTHER INFORMATION: Synthetic oligonucleotide

```
<400> SEQUENCE: 27
gctgcaacag acccggtta                                              19

<210> SEQ ID NO 28
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 28
ctggcgggtc cttctgatt                                              19

<210> SEQ ID NO 29
<211> LENGTH: 29
<212> TYPE: DNA
<213> ORGANISM: Artificial sequence
<220> FEATURE:
<223> OTHER INFORMATION: Synthetic oligonucleotide

<400> SEQUENCE: 29
ccgaagagga acaacacaaa ggacttccc                                   29

<210> SEQ ID NO 30
<211> LENGTH: 26
<212> TYPE: DNA
<213> ORGANISM: Artificial sequence
<220> FEATURE:
<223> OTHER INFORMATION: Synthetic oligonucleotide

<400> SEQUENCE: 30
ttgtcttgaa ttttagcttt gacgtt                                      26

<210> SEQ ID NO 31
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 31
ccttgaccgg aaaaacaatc a                                           21

<210> SEQ ID NO 32
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 32
tcaatggtgt cggagctttc cacttcc                                     27
```

METHODS FOR IDENTIFYING PLANTS WITH EXTENDED SHELF LIFE

This application is a divisional of U.S. application Ser. No. 14/035,756, filed Sep. 24, 2013, which claims the priority of U.S. Provisional Appl. Ser. No. 61/704,602, filed Sep. 24, 2012, the entire disclosures of which are incorporated herein by reference.

INCORPORATION OF SEQUENCE LISTING

The sequence listing that is contained in the file named "SEMB014US_ST25," which is 9 kilobytes as measured in Microsoft Windows operating system and was created on Sep. 24, 2013, is filed electronically herewith and incorporated herein by reference.

BACKGROUND OF THE INVENTION

Field of the Invention

The present invention relates to methods and compositions for improving shelf life of plants and plant parts.

Description of Related Art

Polyphenol oxidases (PPOs) are a group of copper-binding proteins, widely distributed phylogenetically from bacteria to mammals, that catalyze the oxidation of phenolics to quinones which produce brown pigments in wounded tissues. PPO has been implicated in the formation of pigments, oxygen scavenging and defense mechanism against plant pathogens and herbivorous insects. The oxidation of phenolic substrates by PPO is thought to be the major cause of browning coloration of many fruits and vegetables during ripening, handling, storage and processing. This problem is of considerable importance to the food industry as it affects the nutritional quality and appearance, reduces the consumer acceptability and therefore also results in significant economic impact, both to the food producers and to the food processing industry.

SUMMARY OF THE INVENTION

In one aspect, the invention provides compositions for topical application to a plant or part thereof, comprising an amount of a Polyphenol Oxidase 11 (PPO11) inhibitory compound effective to suppress expression of a PPO11 gene or ortholog thereof, wherein expression of the PPO11 gene or ortholog thereof in the absence of the inhibitory compound positively correlates with browning of the plant or part thereof. The composition may also comprise a transfer agent, a buffer, and/or an organosilicone preparation as transfer agent. The PPO11 inhibitory compound may comprise, for example, a sense ssDNA, sense ssRNA, dsRNA, dsDNA, a double stranded DNA/RNA hybrid, anti-sense ssDNA, or anti-sense ssRNA. In certain embodiments, the PPO11 inhibitory compound may comprise an antisense oligonucleotide or dsRNA, or a nucleic acid encoding an antisense oligonucleotide or dsRNA effective to suppress expression of PPO11. In further embodiments, the PPO11 inhibitory compound may comprise a polynucleotide molecule that is at least 18 to about 24, about 25 to about 50, about 51 to about 100, about 101 to about 300, about 301 to about 500, or at least about 500 or more nucleotides in length. In additional embodiments, the plant may be lettuce and the PPO11 gene may be encoded by a sequence comprising SEQ ID NO:9. The PPO11 inhibitory compound may comprise a polynucleotide comprising all or a part of a polynucleotide selected from the group consisting of SEQ ID NOs:1-9, or a complement thereof. In certain embodiments, the amount of PPO11 inhibitory compound is effective to reduce browning, or increase shelf life, of a processed plant product.

In another aspect, the invention provides methods for reducing browning or increasing shelf life of a plant, or part or product thereof, comprising topically applying to a surface of the plant or a part thereof a composition described herein. In certain embodiments, the plant is a potato, apple, spinach, or lettuce plant. In one embodiment, the plant is lettuce, and the PPO inhibitory compound comprises a polynucleotide comprising at least 21 contiguous nucleotides of SEQ ID NO:9, or a complement thereof.

In yet another aspect, the invention provides expression cassettes comprising a selected DNA operably linked to a heterologous promoter, the selected DNA encoding an antisense RNA, including dsRNA sequences, effective to suppress expression of a PPO11 gene or ortholog thereof, wherein expression of the PPO11 gene is positively correlated with browning or reduced shelf life of the plant, or part or product thereof. In certain embodiments, the promoter is a leaf-specific promoter. In various aspects, the selected DNA is operably linked to the promoter in antisense orientation; and/or the PPO11 gene encodes the polypeptide encoded by SEQ ID NO:9; the selected DNA comprises all or a portion of a sequence selected from the group consisting of SEQ ID NOs:1-9. In certain embodiments, expression of the selected DNA induces gene silencing, mRNA cleavage, or repressed translation of mRNA of a PPO11 gene. In further embodiments, the selected DNA is at least 90% identical to at least 200 contiguous nucleotides of SEQ ID NO:9 or a complement thereof; or comprises at least 18, 19, 20, 21, or 22 contiguous nucleotides of SEQ ID NO:334 or a complement thereof; and wherein transcription of the selected DNA suppresses expression of the PPO gene that is positively correlated with browning or reduced shelf life of the plant, or portion or product thereof. The invention also includes vectors comprising the expression cassette described above.

In still yet another aspect, the invention provides transgenic plant comprising the above described expression cassette. In certain embodiments, the plant may be a dicot, a lettuce plant, an R0 transgenic plant, a progeny plant of any generation of an R0 transgenic plant, wherein the transgenic plant has inherited the selected DNA from the R0 transgenic plant, and/or a progeny plant or a plant part derived therefrom that exhibits improved shelf life and reduced postharvest losses.

In still yet another aspect, the invention provides seed of the above described transgenic plant, wherein the seed comprises the expression cassette. In certain embodiments, the seed exhibits an improved shelf life and reduced post-harvest losses. The invention also includes transgenic cells of the above described transgenic plant, wherein the cell comprises the expression cassette, a processed product of the plant or of a progeny thereof, wherein the processed product exhibits an improved shelf life, and the processed product, may be further defined as a head of lettuce, an apple fruit, a potato tuber, or a portion or product thereof.

In certain further aspects, the invention provides methods of down-regulating activity of a PPO11 gene in a plant, the methods comprising introducing into the plant an expression cassette provided by the invention; and selecting a plant with decreased PPO11 activity compared to a plant in which the expression cassette has not been introduced. In certain embodiments, the PPO11 gene encodes mRNA comprising SEQ ID NO:9, and the plant is lettuce. The selected DNA may encode at least 21 continuous nucleotides of a PPO11 mRNA or a complement thereof, effective to down regulate expression of PPO11; the selected DNA may be operably linked to the promoter in the antisense orientation; and/or be in sense and antisense orientation. In certain embodiments, introducing the expression cassette comprises plant breeding and/or genetic transformation. In further embodiments, the polynucleotide may be an antisense or RNAi construct, the selected DNA encodes a ribozyme or zinc-finger protein that inhibits the expression of PPO11. The plant may also be a lettuce, potato, apple, or spinach plant.

In still further aspects, the invention provides methods for making human food comprising obtaining a plant according to the invention, growing the plant under plant growth conditions to produce plant tissue from the plant; and preparing food for human or animal consumption from the plant tissue.

In yet other aspects, the invention provides methods for identifying plants having reduced expression or lacking expression of a PPO11 gene or ortholog thereof, comprising obtaining a plurality of plants, in which expression is positively correlated with browning or reduced shelf life of a processed product of the plant, selecting one or more screened plants comprising decreased expression of the PPO11 gene or ortholog thereof relative to expression of the PPO11 gene or ortholog thereof in a reference plant of the same crop species, a parent plant, or an otherwise isogenic plant, and which displays browning or reduced shelf life. In certain embodiments, the plurality of plants are obtained by random mutagenesis, are transgenic plants, comprise 10, 100, or 1000 or more plants, and/or are varieties of the same species of plants. In certain embodiments, screening for expression of the PPO gene comprises determining an abundance of PPO11 RNA, determining PPO activity, or determining abundance of a protein or RNA encoded by SEQ ID NO:9. In certain embodiment, the method further comprises crossing the one or more plants with reduced expression of PPO11 to a different plant.

In still yet another aspect, the invention provides methods for identifying a polymorphism genetically linked to a PPO11 gene or ortholog thereof, comprising: obtaining DNA of a population of plants wherein members of the population vary for expression of PPO11; and identifying at least a first polymorphism in said population that is associated with a reduced expression of PPO11 relative to members of the population that do not comprise said polymorphism.

In still yet another aspect, the invention provides methods of lettuce breeding comprising assaying lettuce plants, or seeds that produce the lettuce plants, for the presence of at least a first genetic marker genetically linked to a chromosomal region conferring reduced PPO11 expression relative to a plant lacking the region, wherein the region is a low PPO11 expression contributing QTL between 185700k and 185800k on lettuce chromosome 4; and selecting at least a first lettuce plant or seed that produces the plant comprising the genetic marker and the QTL that confers reduced expression of PPO11; and crossing the first plant with itself or a second plant to produce progeny plants comprising the QTL that confers reduced expression of PPO.

In still yet another aspect, the invention provides methods of identifying a lettuce plant that displays reduced browning or increased shelf life comprising: detecting in a first lettuce plant at least one allele of a marker that is associated with reduced browning or increased shelf life, wherein the marker is genetically linked to a region between 185700k and 185800k on lettuce chromosome 4.

BRIEF DESCRIPTION OF THE DRAWINGS

FIG. 3A depicts a strong correlation between PPO11 expression levels 9 days after processing and cold storage with visual discoloration ratings for two crisphead romaine cross and three iceberg varieties grown in San Juan Bautista. Each point represents the least square mean for a single cultivar with six biological replicates for both gene expression and visual ratings. FIG. 3B is a validation experiment with 10 cultivars grown in Yuma, Ariz. again demonstrating a statistically significant correlation between PPO11 expression levels 9 days after processing and cold storage with visual discoloration ratings for two crisphead romaine cross, three iceberg, and five Romaine cultivars. Each point represents the least square mean for a single cultivar with six biological replicates for both gene expression and visual ratings. Iceberg "ICE", crisphead-romaine cross "CRC," and romaine "R0M" lettuce.

BRIEF DESCRIPTION OF THE SEQUENCE LISTING

Figure 1:
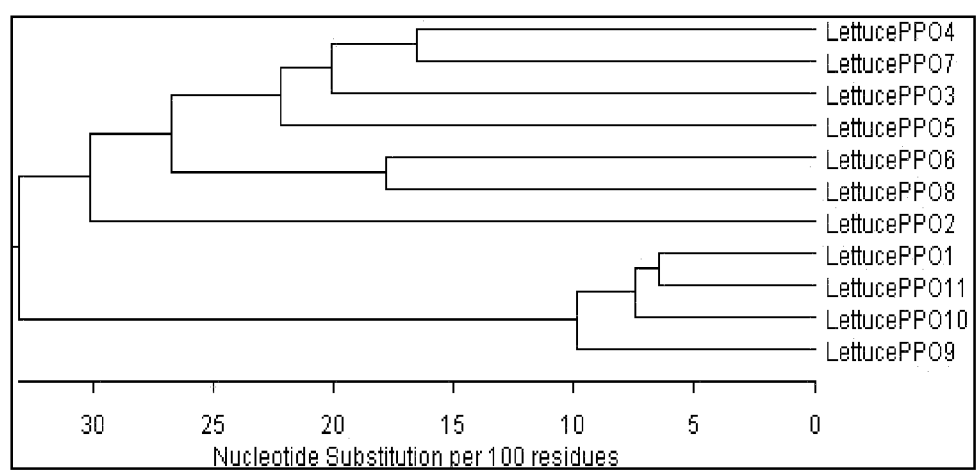
FIG. 1: Eleven putative PPO genes exist in lettuce. Based on analysis of nucleotide substitution per 100 nucleotide residues, the relative level of homology among the PPO genes is shown.

SEQ ID NO:1—PPO11_Trigger1 sequence (189 nt).
SEQ ID NO:2—PPO11_Trigger2 (225 nt).

SEQ ID NO:3—PPO11_Trigger3 (225 nt).
SEQ ID NO:4—PPO11_Trigger4 (226 nt).
SEQ ID NO:5—PPO11_antisense ssDNA (25 nt).
SEQ ID NO:6—PPO11_antisense ssDNA (25 nt).
SEQ ID NO:7—PPO11_dsRNA (25 nt).
SEQ ID NO:8—PPO11_dsRNA (25 nt).
SEQ ID NO:9—*Lactuca sativa* (lettuce) deduced PPO11 mRNA (1922 nt).
SEQ ID NO:10—PPO11 flanking sequence (Sequence Chr4:185719000-185720000).
SEQ ID NO:11—PPO11 flanking sequence (Sequence Chr4:1185723000-185724000).
SEQ ID NOs:12-34—Gene-specific PCR primers.

DETAILED DESCRIPTION OF THE INVENTION

Polyphenol oxidases (PPOs) are a group of copper-binding proteins, widely distributed phylogenetically from bacteria to mammals that catalyze the oxidation of phenolics to quinones and produce brown pigments in wounded tissues. The present invention overcomes the limitations of the prior art by providing novel methods, compositions, and plants for extending shelf life of plant products by specific reduction of expression of a PPO that positively correlates with browning in plants. PPO11 of lettuce provides a non-limiting example of a PPO that correlates with browning in lettuce. It was recognized that expression of PPO11 increases over time after harvest and correlates with reduced shelf life and increased browning. Compositions are disclosed that comprise selective PPO inhibitory compounds to inhibit a specific PPO that positively correlates with browning such as PPO11, and methods to reduce browning or increase shelf life. Also disclosed are expression cassettes and vectors comprising a selected DNA whose expression is effective to suppress expression of PPO11, reduce browning, and/or increase shelf life of plants or plant parts. Transgenic plants or plants comprising PPO11 inhibitory compounds and methods of producing such are also disclosed. Plants or plant varieties that harbor a PPO gene or promoter mutations that result in reduced PPO gene expression and methods of assaying PPO gene expression as a proxy for browning are also disclosed herein. In particular embodiments, the PPO gene that positively correlates with browning is a PPO11 gene from lettuce and/or the corresponding ortholog from apple or potato. In addition, methods of producing PPO genes with reduced expression are provided.

Definitions

In the description and tables herein, a number of terms are used. In order to provide a clear and consistent understanding of the specification and claims, the following definitions are provided. Unless otherwise noted, terms are to be understood according to conventional usage by those of ordinary skill in the relevant art.

Where a term is provided in the singular, the inventors also contemplate aspects of the invention described by the plural of that term.

As used herein, the term "selective PPO inhibitory compound" refers to a compound that suppresses or reduces an activity of PPO enzymatic activity, or expression of PPO, such as for example synthesis of mRNA encoding a PPO polypeptide (transcription) and/or synthesis of a PPO polypeptide from PPO mRNA (translation). In some embodiments the selective PPO inhibitory compound specifically inhibits a PPO that positively correlates with browning of the plant. In certain embodiments, the PPO inhibitory compound is an inhibitor of PPO11 or the corresponding gene in apple or potatoes.

As used herein, a PPO that positively correlates with browning of the plant refers to a specific PPO homolog that exhibits an increase of expression after harvest when the browning/discoloration increases or occurs. In certain embodiments, the increase of expression is observed during the period of 36 hrs after harvest. The PPO that positively correlates with browning of the plant (plant surface or parts of a plant) also exhibits an increase of expression that correlates with visual discoloration of the plant surface. In certain embodiments, such PPO is PPO11. In certain embodiments, the PPO is a homolog of PPO11 of lettuce correlated with the presence of browning, such as from apple or potato, which may therefore be targeted for reduction of browning.

As used herein, the term "expression cassette" refers to a DNA sequence that comprises a selected DNA to be transcribed. In addition, the expression cassette comprises at least all DNA elements required for expression. After successful transformation, the expression cassette directs the cell's machinery to make RNA. In certain embodiments, the expression cassette is an iRNA or siRNA expression cassette that suppresses expression of a PPO that positively correlates with browning of a plant.

Different expression cassettes can be transformed into different organisms including bacteria, yeast, plants, and mammalian cells as long as the correct regulatory sequences are used.

As used herein, the term "abundance of a protein" refers to the amount of the specific protein relative to the amount of total protein or relative to the weight or volume of the cell, tissue, plant, or plant part tested.

As used herein, the term "abundance of a mRNA" refers to the amount of the specific mRNA relative to the amount of total protein or relative to the weight or volume of the cell, tissue, plant, or plant part tested.

As used herein, the term "expression" refers to the combination of intracellular processes, including transcription and translation undergone by a coding DNA molecule such as a structural gene to produce a polypeptide.

As used herein, the term "genetic transformation" refers to process of introducing a DNA sequence or construct (e.g., a vector or expression cassette) into a cell or protoplast in which that exogenous DNA is incorporated into a chromosome or is capable of autonomous replication.

As used herein, the term "heterologous" refers to a sequence which is not normally present in a given host genome in the genetic context in which the sequence is currently found In this respect, the sequence may be native to the host genome, but be rearranged with respect to other genetic sequences within the host sequence. For example, a regulatory sequence may be heterologous in that it is linked to a different coding sequence relative to the native regulatory sequence.

As used herein, the term "obtaining" when used in conjunction with a transgenic plant cell or transgenic plant, means either for 1) transforming a non-transgenic plant cell or plant to create the transgenic plant cell or plant, or for 2) planting transgenic plant seed to produce the transgenic plant cell or plant. Such a transgenic plant seed may be from an $R_0$ transgenic plant or may be from a progeny of any generation thereof that inherits a given transgenic sequence from a starting transgenic parent plant.

As used herein, the term "promoter" refers to a recognition site on a DNA sequence or group of DNA sequences that provides an expression control element for a structural gene and to which RNA polymerase specifically binds and initiates RNA synthesis (transcription) of that gene As used herein, the term "$R_0$ transgenic plant" refers to a plant that has been genetically transformed or has been regenerated from a plant cell or cells that have been genetically transformed.

As used herein, the term "regeneration" refers to the process of growing a plant from a plant cell (e.g., plant protoplast, callus or explant).

As used herein, the term "transformation construct" refers to a chimeric DNA molecule which is designed for introduction into a host genome by genetic transformation. Preferred transformation constructs will comprise all of the genetic elements necessary to direct the expression of one or more exogenous genes. In particular embodiments of the instant invention, it may be desirable to introduce a transformation construct into a host cell in the form of an expression cassette.

As used herein, the term "transformed cell" refers to a cell the DNA complement of which has been altered by the introduction of an exogenous DNA molecule into that cell.

As used herein, the term "transgene" refers to a segment of DNA which has been incorporated into a host genome or is capable of autonomous replication in a host cell and is capable of causing the expression of one or more coding sequences. Exemplary transgenes will provide the host cell, or plants regenerated therefrom, with a novel phenotype relative to the corresponding non-transformed cell or plant. Transgenes may be directly introduced into a plant by genetic transformation, or may be inherited from a plant of any previous generation which was transformed with the DNA segment.

As used herein, the term "transgenic plant" refers to a plant or progeny plant of any subsequent generation derived therefrom, wherein the DNA of the plant or progeny thereof contains an introduced exogenous DNA segment not naturally present in a non-transgenic plant of the same strain. The transgenic plant may additionally contain sequences which are native to the plant being transformed, but wherein the "exogenous" gene has been altered in order to alter the level or pattern of expression of the gene, for example, by use of one or more heterologous regulatory or other elements.

As used herein, the term "vector" refers to a DNA molecule designed for transformation into a host cell. Some vectors may be capable of replication in a host cell. A plasmid is an exemplary vector, as are expression cassettes isolated therefrom.

As used herein, the terms "DNA," "DNA molecule," and "DNA polynucleotide molecule" refer to a single-stranded DNA or double-stranded DNA molecule of genomic or synthetic origin, such as, a polymer of deoxyribonucleotide bases or a DNA polynucleotide molecule.

As used herein, the terms "DNA sequence," "DNA nucleotide sequence," and "DNA polynucleotide sequence" refer to the nucleotide sequence of a DNA molecule. ssDNA refers to single-stranded DNA; dsDNA refers to double-stranded DNA.

As used herein, the term "gene" refers to any portion of a nucleic acid that provides for expression of a transcript or encodes a transcript. A "gene" thus includes, but is not limited to, a promoter region, 5' untranslated regions, transcript encoding regions that can include intronic regions, and 3' untranslated regions.

As used herein, the terms "RNA," "RNA molecule," and "RNA polynucleotide molecule" refer to a single-stranded RNA or double-stranded RNA molecule of genomic or synthetic origin, such as, a polymer of ribonucleotide bases that comprise single or double stranded regions. ssRNA specifically refers to single-stranded RNA; ds refers to double-stranded RNA.

Unless otherwise stated, nucleotide sequences in the text of this specification are given, when read from left to right, in the 5' to 3' direction. The nomenclature used herein is that required by Title 37 of the United States Code of Federal Regulations § 1.822 and set forth in the tables in WIPO Standard ST.25 (1998), Appendix 2, Tables 1 and 3.

As used herein, a "plant surface" refers to any exterior portion of a plant. Plant surfaces thus include, but are not limited to, the surfaces of flowers, stems, tubers, fruit, anthers, pollen, leaves, roots, or seeds. A plant surface can be on a portion of a plant that is attached to other portions of a plant or on a portion of a plant that is detached from the plant.

As used herein, the phrase "polynucleotide is not operably linked to a promoter" refers to a polynucleotide that is not covalently linked to a polynucleotide promoter sequence that is specifically recognized by either a DNA dependent RNA polymerase II protein or by a viral RNA dependent RNA polymerase in such a manner that the polynucleotide will be transcribed by the DNA dependent RNA polymerase II protein or viral RNA dependent RNA polymerase. A polynucleotide that is not operably linked to a promoter can be transcribed by a plant RNA dependent RNA polymerase.

As used herein, a polynucleotides may be in the form of ssDNA, encompass dsDNA equivalents, dsRNA equivalents, ssRNA equivalents, ssRNA complements, ssDNA as shown, and ssDNA complements.

As used herein, a first nucleic-acid sequence, selected DNA, or polynucleotide is "operably" connected or "linked" with a second nucleic acid sequence when the first nucleic acid sequence is placed in a functional relationship with the second nucleic acid sequence. For instance, a promoter is operably linked to an RNA and/or protein-coding sequence, or a sequence encoding an iRNA, an siRNA, or a nucleic acid encoding an antisense oligonucleotide if the promoter provides for transcription or expression of the RNA or coding sequence. Generally, operably linked DNA sequences are contiguous and, where necessary to join two protein-coding regions, are in the same reading frame. Selected DNA refers to a DNA segment which one desires to introduce or has introduced into a plant genome by genetic transformation In certain embodiment, the selected DNA is an antisense or RNAi construct. In another embodiment, the selected DNA encodes a ribozyme, or zinc-finger protein.

As used herein, the phrase "organosilicone preparation" refers to a liquid comprising one or more organosilicone compounds, wherein the liquid or components contained therein, when combined with a polynucleotide in a composition that is topically applied to a target plant surface, enable the polynucleotide to enter a plant cell. Exemplary organosilicone preparations include, but are not limited to, preparations marketed under the trade names "Silwet®" or "BREAK-THRU®" and preparations provided in the following Table. In certain embodiments, an organosilicone preparation can enable a polynucleotide to enter a plant cell in a manner permitting a polynucleotide mediated suppression of target gene expression in the plant cell.

As used herein, the phrases "reduced browning," "increased shelf life," "improved shelf life," "reduced post-harvest losses," or "improving shelf life and reducing post-harvest losses" refer to any measurable increase in shelf life, reduction in browning, or reduction in postharvest loss observed in a plant or part thereof subjected to the present invention when compared to the plant or part thereof not subjected to the present invention. In certain embodiments, an increase in shelf life or reduction in postharvest loss in a plant or plant part can be determined in a comparison to a control plant or plant part that has not been treated with a composition comprising a polynucleotide and a transfer agent. When used in this context, a control plant is a plant that has not undergone treatment with a PPO inhibitory compound or a polynucleotide, non-transgenic plants, or plants not exhibiting reduced expression of a PPO. Such control plants would include, but are not limited to, untreated plants or mock treated plants. In certain embodiments, the phrases relate to non-transgenic plants or plants that do not comprise an expression cassette that effectively suppresses PPO activity.

As used herein, the phrase "provides for a reduction," "effective to suppress," and "effectively suppresses" when used in the context of a transcript or a protein in a plant or plant part, refers to any measurable decrease in the level of transcript or protein in a plant or plant part. Thus, expression of a gene can be suppressed when there is a reduction in levels of a transcript from the gene, a reduction in levels of a protein encoded by the gene, a reduction in the activity of the transcript from the gene, a reduction in the activity of a protein encoded by the gene, any one of the preceding conditions, or any combination of the preceding conditions. In this context, the activity of a transcript includes, but is not limited to, its ability to be translated into a protein and/or to exert any RNA-mediated biologic or biochemical effect. In this context, the activity of a protein includes, but is not limited to, its ability to exert any protein-mediated biologic or biochemical effect. In certain embodiments, a suppression of gene expression in a plant or plant part can be determined in a comparison of gene product levels or activities in a treated plant to a control plant or plant part that has not been treated with a composition comprising a polynucleotide and a transfer agent. When used in this context, a control plant or plant part is a plant or plant part that has not undergone treatment with polynucleotide and a transfer agent. Such control plants or plant parts would include, but are not limited to, untreated or mock treated plants and plant parts. In certain embodiments, a reduction of the level of a transcript or protein in a plant or plant part can be determined in a comparison to a control plant or plant part that has not been treated with a composition comprising a polynucleotide and a transfer agent. When used in this context, a control plant or plant part is a plant or plant part that has not undergone treatment with a PPO inhibitory compound, a polynucleotide. Such control plants or plant parts would include, but are not limited to, untreated or mock treated plants and plant parts. In certain embodiments, the phrases relate to non-transgenic plants or plants that do not comprise an expression cassette that having the continuous nucleotides of a PPO gene, or a plant that does not comprise a transgene.

As used herein, the phrase "wherein said plant does not comprise a transgene" refers to a plant that lacks either a DNA molecule comprising a promoter that is operably linked to a polynucleotide or a recombinant viral vector.

As used herein, the term "transcript" corresponds to any RNA that is produced from a gene by the process of transcription. A transcript of a gene can thus comprise a primary transcription product which can contain introns or can comprise a mature RNA that lacks introns.

As used herein, "polynucleotide" may refer to a DNA or RNA molecule containing multiple nucleotides and generally refers both to "oligonucleotides" (a polynucleotide molecule of 18-25 nucleotides in length) and longer polynucleotides of 26 or more nucleotides. Embodiments of this invention include compositions including oligonucleotides having a length of 18-25 nucleotides (18-mers, 19-mers, 20-mers, 21-mers, 22-mers, 23-mers, 24-mers, or 25-mers), and longer, or medium-length polynucleotides having a length of 26 or more nucleotides (polynucleotides of 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, about 65, about 70, about 75, about 80, about 85, about 90, about 95, about 100, about 110, about 120, about 130, about 140, about 150, about 160, about 170, about 180, about 190, about 200, about 210, about 220, about 230, about 240, about 250, about 260, about 270, about 280, about 290, or about 300 nucleotides), or long polynucleotides having a length greater than about 300 nucleotides (e.g., polynucleotides of between about 300 to about 400 nucleotides, between about 400 to about 500 nucleotides, between about 500 to about 600 nucleotides, between about 600 to about 700 nucleotides, between about 700 to about 800 nucleotides, between about 800 to about 900 nucleotides, between about 900 to about 1000 nucleotides, between about 300 to about 500 nucleotides, between about 300 to about 600 nucleotides, between about 300 to about 700 nucleotides, between about 300 to about 800 nucleotides, between about 300 to about 900 nucleotides, or about 1000 nucleotides in length, or even greater than about 1000 nucleotides in length, for example up to the entire length of a target Polyphenol oxidase (PPO) gene, such as PPO11 including coding or non-coding or both coding and non-coding portions of the target Polyphenol oxidase (PPO) gene). Where a polynucleotide is double-stranded, its length can be similarly described in terms of base pairs.

Polynucleotide compositions used in the various embodiments of this invention include compositions including oligonucleotides, polynucleotides, or a mixture of both, including: RNA or DNA or RNA/DNA hybrids or chemically modified oligonucleotides or polynucleotides or a mixture thereof. In certain embodiments, the polynucleotide may be a combination of ribonucleotides and deoxyribonucleotides, for example, synthetic polynucleotides consisting mainly of ribonucleotides but with one or more terminal deoxyribonucleotides or synthetic polynucleotides consisting mainly of deoxyribonucleotides but with one or more terminal dideoxyribonucleotides. In certain embodiments, the polynucleotide includes non-canonical nucleotides such as inosine, thiouridine, or pseudouridine. In certain embodiments, the polynucleotide includes chemically modified nucleotides. Examples of chemically modified oligonucleotides or polynucleotides are well known in the art; see, for example, U.S. Patent Publication 2011/0171287, U.S. Patent Publication 2011/0171176, U.S. Patent Publication 2011/0152353, U.S. Patent Publication 2011/0152346, and U.S. Patent Publication 2011/0160082, which are herein incorporated by reference. Illustrative examples include, but are not limited to, the naturally occurring phosphodiester backbone of an oligonucleotide or polynucleotide which can be partially or completely modified with phosphorothioate, phosphorodithioate, or methylphosphonate internucleotide linkage modifications, modified nucleoside bases or modified sugars can be used in oligonucleotide or polynucleotide synthesis, and oligonucleotides or polynucleotides can be labeled with a fluorescent moiety (e.g., fluorescein or rhodamine) or other label (e.g., biotin).

Polynucleotides can be single- or double-stranded RNA, single- or double-stranded DNA, double-stranded DNA/

RNA hybrids, and modified analogues thereof. In certain embodiments of the invention, the polynucleotides that provide single-stranded RNA in the plant cell may be: (a) a single-stranded RNA molecule (ssRNA), (b) a single-stranded RNA molecule that self-hybridizes to form a double-stranded RNA molecule, (c) a double-stranded RNA molecule (dsRNA), (d) a single-stranded DNA molecule (ssDNA), (e) a single-stranded DNA molecule that self-hybridizes to form a double-stranded DNA molecule, (f) a single-stranded DNA molecule including a modified Pol III gene that is transcribed to an RNA molecule, (g) a double-stranded DNA molecule (dsDNA), (h) a double-stranded DNA molecule including a modified Pol III gene that is transcribed to an RNA molecule, and (i) a double-stranded, hybridized RNA/DNA molecule, or combinations thereof. In certain embodiments, these polynucleotides can comprise both ribonucleic acid residues and deoxyribonucleic acid residues. In certain embodiments, these polynucleotides include chemically modified nucleotides or non-canonical nucleotides. In certain embodiments of the methods, the polynucleotides include double-stranded DNA formed by intramolecular hybridization, double-stranded DNA formed by intermolecular hybridization, double-stranded RNA formed by intramolecular hybridization, or double-stranded RNA formed by intermolecular hybridization. In certain embodiments where the polynucleotide is a dsRNA, the anti-sense strand will comprise at least 18 nucleotides that are essentially complementary to the target Polyphenol oxidase (PPO) gene. In certain embodiments the polynucleotides include single-stranded DNA or single-stranded RNA that self-hybridizes to form a hairpin structure having an at least partially double-stranded structure including at least one segment that will hybridize to RNA transcribed from the gene targeted for suppression. Not intending to be bound by any mechanism, it is believed that such polynucleotides are or will produce single-stranded RNA with at least one segment that will hybridize to RNA transcribed from the gene targeted for suppression. In certain embodiments, the polynucleotides can be operably linked to a promoter— generally a promoter functional in a plant, for example, a pol II promoter, a pol III promoter, a pol IV promoter, or a pol V promoter.

The polynucleotide molecules of the present invention are designed to modulate expression by inducing regulation or suppression of an endogenous Polyphenol oxidase (PPO) gene, such as PPO11, to reduce expression of PPO11 in a plant and are designed to have a nucleotide sequence essentially identical or essentially complementary to the nucleotide sequence of an endogenous Polyphenol oxidase (PPO) gene of a plant or to the sequence of RNA transcribed from an endogenous Polyphenol oxidase (PPO) gene of a plant, which can be coding sequence or non-coding sequence. These effective polynucleotide molecules that modulate expression are referred to herein as "a trigger, or triggers". By "essentially identical" or "essentially complementary" it is meant that the trigger polynucleotides (or at least one strand of a double-stranded polynucleotide) have sufficient identity or complementarity to the endogenous gene or to the RNA transcribed from the endogenous Polyphenol oxidase (PPO) gene (e.g., the transcript) to suppress expression of the endogenous Polyphenol oxidase (PPO) gene (e.g., to effect a reduction in levels or activity of the gene transcript and/or encoded protein). In certain embodiments, the trigger polynucleotides provided herein can be directed to a Polyphenol oxidase (PPO) transgene present in the plant. Polynucleotides of the methods and compositions provided herein need not have 100 percent identity to a complementarity to the endogenous Polyphenol oxidase (PPO) gene or to the RNA transcribed from the endogenous Polyphenol oxidase (PPO) gene (i.e., the transcript) to suppress expression of the endogenous Polyphenol oxidase (PPO) gene (i.e., to effect a reduction in levels or activity of the gene transcript or encoded protein). Thus, in certain embodiments, the polynucleotide or a portion thereof is designed to be essentially identical to, or essentially complementary to, a sequence of at least 18 or 19 contiguous nucleotides in either the target gene or messenger RNA transcribed from the target gene (e.g., the transcript). In certain embodiments, an "essentially identical" polynucleotide has 100 percent sequence identity or at least about 83, 84, 85, 86, 87, 88, 89, 90, 91, 92, 93, 94, 95, 96, 97, 98, or 99 percent sequence identity when compared to the sequence of 18 or more contiguous nucleotides in either the endogenous target gene or to an RNA transcribed from the target gene (e.g., the transcript). In certain embodiments, an "essentially complementary" polynucleotide has 100 percent sequence complementarity or at least about 83, 84, 85, 86, 87, 88, 89, 90, 91, 92, 93, 94, 95, 96, 97, 98, or 99 percent sequence complementarity when compared to the sequence of 18 or more contiguous nucleotides in either the target gene or RNA transcribed from the target gene.

In certain embodiments, polynucleotides used in the methods and compositions provided herein can be essentially identical or essentially complementary to any of: i) conserved regions of Polyphenol oxidase (PPO) genes of both monocot and dicot plants; ii) conserved regions of Polyphenol oxidase (PPO) genes of monocot plants; or iii) conserved regions of Polyphenol oxidase (PPO) genes of dicot plants. Such polynucleotides that are essentially identical or essentially complementary to such conserved regions can be used to improve shelf life and reduce postharvest losses by suppressing expression of Polyphenol oxidase (PPO) genes in various dicot and/or monocot plants.

Polynucleotides containing mismatches to the target gene or transcript can thus be used in certain embodiments of the compositions and methods provided herein. In certain embodiments, a polynucleotide can comprise at least 19 contiguous nucleotides that are essentially identical or essentially complementary to said gene or said transcript or comprises at least 19 contiguous nucleotides that are essentially identical or essentially complementary to the target gene or target gene transcript. In certain embodiments, a polynucleotide of 19 continuous nucleotides that is essentially identical or essentially complementary to the endogenous target gene or to a RNA transcribed from the target gene (e.g., the transcript) can have 1 or 2 mismatches to the target gene or transcript. In certain embodiments, a polynucleotide of 20 or more nucleotides that contains a contiguous 19 nucleotide span of identity or complementarity to the endogenous target gene or to an RNA transcribed from the target gene can have 1 or 2 mismatches to the target gene or transcript. In certain embodiments, a polynucleotide of 21 continuous nucleotides that is essentially identical or essentially complementary to the endogenous target gene or to an RNA transcribed from the target gene (e.g., the transcript) can have 1, 2, or 3 mismatches to the target gene or transcript. In certain embodiments, a polynucleotide of 22 or more nucleotides that contains a contiguous 21 nucleotide span of identity or complementarity to the endogenous target gene or to an RNA transcribed from the target gene can have 1, 2, or 3 mismatches to the target gene or transcript. In designing polynucleotides with mismatches to an endogenous target gene or to an RNA transcribed from the target gene, mismatches of certain types and at certain positions that are more likely to be tolerated can be used. In certain exemplary embodiments, mismatches formed between adenine and cytosine or guanosine and uracil residues are used as described by Du et al. Nucleic Acids Research, 2005, Vol. 33, No. 5 1671-1677. In certain exemplary embodiments, mismatches in 19 base pair overlap regions can be at the low tolerance positions 5, 7, 8 or 11 (from the 5' end of a 19 nucleotide target) with well tolerated nucleotide mismatch residues, at medium tolerance positions 3, 4, and 12-17, and/or at the high tolerance nucleotide positions at either end of the region of complementarity (i.e., positions 1, 2, 18, and 19) as described by Du et al. Nucleic Acids Research, 2005, Vol. 33, No. 5 1671-1677. It is further anticipated that tolerated mismatches can be empirically determined in assays where the polynucleotide is applied to the plants via the methods provided herein and the treated plants assayed for suppression of Polyphenol oxidase (PPO) gene expression or appearance of improved shelf life and reduced postharvest losses.

In certain embodiments, polynucleotide molecules are designed to have 100 percent sequence identity with or complementarity to one allele or one family member of a given target Polyphenol oxidase (PPO) gene coding or non-coding sequence. Target Polyphenol oxidase (PPO) genes include both the Polyphenol oxidase (PPO) genes of SEQ ID NO:1-23 as well as orthologous Polyphenol oxidase (PPO) genes obtainable from other crops. In other embodiments, the polynucleotide molecules are designed to have 100 percent sequence identity with or complementarity to multiple alleles or family members of a given target gene.

In certain embodiments, polynucleotide compositions and methods provided herein typically effect regulation or modulation (e. g., suppression) of gene expression during a period during the life of the treated plant of at least 1 week or longer and typically in systemic fashion. For instance, within days of treating a plant leaf with a polynucleotide composition of this invention, primary and transitive siRNAs can be detected in other leaves lateral to and above the treated leaf and in apical tissue. In certain embodiments, methods of systemically suppressing expression of a gene in a plant, the methods comprising treating said plant with a composition comprising at least one polynucleotide and a transfer agent, wherein said polynucleotide comprises at least 18 or at least 19 contiguous nucleotides that are essentially identical or essentially complementary to a gene or a transcript encoding a Polyphenol oxidase (PPO) gene of the plant are provided, whereby expression of the gene in said plant or progeny thereof is systemically suppressed in comparison to a control plant that has not been treated with the composition.

Compositions used to suppress a target gene can comprise one or more polynucleotides that are essentially identical or essentially complementary to multiple genes, or to multiple segments of one or more genes. In certain embodiments, compositions used to suppress a target gene can comprise one or more polynucleotides that are essentially identical or essentially complementary to multiple consecutive segments of a target gene, multiple non-consecutive segments of a target gene, multiple alleles of a target gene, or multiple target genes from one or more species.

In certain embodiments, the polynucleotide includes two or more copies of a nucleotide sequence (of 18 or more nucleotides) where the copies are arranged in tandem fashion. In another embodiment, the polynucleotide includes two or more copies of a nucleotide sequence (of 18 or more nucleotides) where the copies are arranged in inverted repeat fashion (forming an at least partially self-complementary strand). The polynucleotide can include both tandem and inverted-repeat copies. Whether arranged in tandem or inverted repeat fashion, each copy can be directly contiguous to the next, or pairs of copies can be separated by an optional spacer of one or more nucleotides. The optional spacer can be unrelated sequence (i.e., not essentially identical to or essentially complementary to the copies, nor essentially identical to, or essentially complementary to, a sequence of 18 or more contiguous nucleotides of the endogenous target gene or RNA transcribed from the endogenous target gene). Alternatively the optional spacer can include sequence that is complementary to a segment of the endogenous target gene adjacent to the segment that is targeted by the copies. In certain embodiments, the polynucleotide includes two copies of a nucleotide sequence of between about 20 to about 30 nucleotides, where the two copies are separated by a spacer no longer than the length of the nucleotide sequence.

Tiling

Polynucleotide trigger molecules can be identified by "tiling" gene targets in random length fragments, e.g., 200-300 polynucleotides in length, with partially overlapping regions, e.g., 25 or so nucleotide overlapping regions along the length of the target gene. Multiple gene target sequences can be aligned and polynucleotide sequence regions with homology in common are identified as potential trigger molecules for multiple targets. Multiple target sequences can be aligned and sequence regions with poor homology are identified as potential trigger molecules for selectively distinguishing targets. To selectively suppress a single gene, trigger sequences may be chosen from regions that are unique to the target gene either from the transcribed region or the non-coding regions, e.g., promoter regions, 3' untranslated regions, introns and the like.

Polynucleotide fragments are designed along the length of the full length coding and untranslated regions of a Polyphenol oxidase (PPO) gene or family member as contiguous overlapping fragments of 200-300 polynucleotides in length or fragment lengths representing a percentage of the target Polyphenol oxidase (PPO) gene. These fragments are applied topically (as sense or anti-sense ssDNA or ssRNA, dsRNA, or dsDNA) to determine the relative effectiveness in providing the improved shelf life and reduced postharvest losses phenotype. Fragments providing the desired activity may be further subdivided into 50-60 polynucleotide fragments which are evaluated for providing the improved shelf life and reduced postharvest losses phenotype. The 50-60 base fragments with the desired activity may then be further subdivided into 19-30 base fragments which are evaluated for providing the improved shelf life and reduced postharvest losses phenotype. Once relative effectiveness is determined, the fragments are utilized singly, or in combination in one or more pools to determine effective trigger composition or mixture of trigger polynucleotides for providing the improved shelf life and reduced postharvest losses phenotype.

Coding and/or non-coding sequences of Polyphenol oxidase (PPO) gene families in the crop of interest are aligned and 200-300 polynucleotide fragments from the least homologous regions amongst the aligned sequences are evaluated using topically applied polynucleotides (as sense or anti-sense ssDNA or ssRNA, dsRNA, or dsDNA) to determine their relative effectiveness in providing the improved shelf life and reduced postharvest losses phenotype. The effective segments are further subdivided into 50-60 polynucleotide fragments, prioritized by least homology, and reevaluated using topically applied polynucleotides. The effective 50-60 polynucleotide fragments are subdivided into 19-30 polynucleotide fragments, prioritized by least homology, and again evaluated for induction of the improved shelf life and reduced postharvest losses phenotype. Once relative effectiveness is determined, the fragments are utilized singly, or again evaluated in combination with one or more other fragments to determine the trigger composition or mixture of trigger polynucleotides for providing the yield/quality phenotype.

Coding and/or non-coding sequences of Polyphenol oxidase (PPO) gene families in the crop of interest are aligned and 200-300 polynucleotide fragments from the most homologous regions amongst the aligned sequences are evaluated using topically applied polynucleotides (as sense or anti-sense ssDNA or ssRNA, dsRNA, or dsDNA) to determine their relative effectiveness in inducing the improved shelf life and reduced postharvest losses phenotype. The effective segments are subdivided into 50-60 polynucleotide fragments, prioritized by most homology, and reevaluated using topically applied polynucleotides. The effective 50-60 polynucleotide fragments are subdivided into 19-30 polynucleotide fragments, prioritized by most homology, and again evaluated for induction of the improved shelf life and reduced postharvest losses phenotype. Once relative effectiveness is determined, the fragments may be utilized singly, or in combination with one or more other fragments to determine the trigger composition or mixture of trigger polynucleotides for providing the improved shelf life and reduced postharvest losses phenotype.

Also, provided herein are methods for identifying a preferred polynucleotide for providing improved shelf life and reduced postharvest losses in a plant. Populations of candidate polynucleotides that are essentially identical or essentially complementary to a Polyphenol oxidase (PPO) gene or transcript of the Polyphenol oxidase (PPO) gene can be generated by a variety of approaches, including but not limited to, any of the tiling, least homology, or most homology approaches provided herein. Such populations of polynucleotides can also be generated or obtained from any of the polynucleotides or genes provided herewith provided in the sequence listing. Such populations of polynucleotides can also be generated or obtained from any genes that are orthologous to the genes provided herewith in the sequence listing. Such polynucleotides can be topically applied to a surface of plants in a composition comprising at least one polynucleotide from said population and a transfer agent to obtain treated plants. Treated plants that exhibit suppression of the Polyphenol oxidase (PPO) gene and/or exhibit an improvement in improved shelf life and reduced postharvest losses are identified, thus identifying a preferred polynucleotide that improves improved shelf life and reduced postharvest losses in a plant. Suppression of the Polyphenol oxidase (PPO) gene can be determined by any assay for the levels and/or activity of a Polyphenol oxidase (PPO) gene product (i.e., transcript or protein). Suitable assays for transcripts include, but are not limited to, semi-quantitative or quantitative reverse transcriptase PCR® (qRT-PCR) assays. Suitable assays for proteins include, but are not limited to, semi-quantitative or quantitative immunoassays, biochemical activity assays, or biological activity assays. In certain embodiments, the polynucleotides can be applied alone. In other embodiments, the polynucleotides can be applied in pools of multiple polynucleotides. When a pool of polynucleotides provides for suppression of the Polyphenol oxidase (PPO) gene and/or an improvement in improved shelf life and reduced postharvest losses are identified, the pool can be de-replicated and retested as necessary or desired to identify one or more preferred polynucleotide(s) that improve improved shelf life and reduced postharvest losses in a plant.

Methods of making polynucleotides are well known in the art. Such methods of making polynucleotides can include in vivo biosynthesis, in vitro enzymatic synthesis, or chemical synthesis. In certain embodiments, RNA molecules can be made by either in vivo or in vitro synthesis from DNA templates where a suitable promoter is operably linked to the polynucleotide and a suitable DNA—dependent RNA polymerase is provided. DNA—dependent RNA polymerases include, but are not limited to, E. coli or other bacterial RNA polymerases as well as the bacteriophage RNA polymerases such as the T7, T3, and SP6 RNA polymerases. Commercial preparation of oligonucleotides often provides two deoxyribonucleotides on the 3' end of the sense strand. Long polynucleotide molecules can be synthesized from commercially available kits, for example, kits from Applied Biosystems/Ambion (Austin, Tex.) have DNA ligated on the 5' end that encodes a bacteriophage T7 polymerase promoter that makes RNA strands that can be assembled into a dsRNA. Alternatively, dsRNA molecules can be produced from expression cassettes in bacterial cells that have regulated or deficient RNase III enzyme activity. Long polynucleotide molecules can also be assembled from multiple RNA or DNA fragments. In some embodiments design parameters such as Reynolds score (Reynolds et al. Nature Biotechnology 22, 326-330 (2004) and Tuschl rules (Pei and Tuschl, Nature Methods 3(9): 670-676, 2006) are known in the art and are used in selecting polynucleotide sequences effective in gene silencing. In some embodiments random design or empirical selection of polynucleotide sequences is used in selecting polynucleotide sequences effective in gene silencing. In some embodiments the sequence of a polynucleotide is screened against the genomic DNA of the intended plant to minimize unintentional silencing of other genes.

While there is no upper limit on the concentrations and dosages of polynucleotide molecules that can be useful in the methods and compositions provided herein, lower effective concentrations and dosages will generally be sought for efficiency. The concentrations can be adjusted in consideration of the volume of spray or treatment applied to plant leaves or other plant part surfaces, such as flower petals, stems, tubers, fruit, anthers, pollen, leaves, roots, or seeds. In one embodiment, a useful treatment for herbaceous plants using 25-mer polynucleotide molecules is about 1 nanomole (nmol) of polynucleotide molecules per plant, for example, from about 0.05 to 1 nmol polynucleotides per plant. Other embodiments for herbaceous plants include useful ranges of about 0.05 to about 100 nmol, or about 0.1 to about 20 nmol, or about 1 nmol to about 10 nmol of polynucleotides per plant. In certain embodiments, about 40 to about 50 nmol of a ssDNA polynucleotide is applied. In certain embodiments, about 0.5 nmol to about 2 nmol of a dsRNA is applied. In certain embodiments, a composition containing about 0.5 to about 2.0 mg/mL, or about 0.14 mg/mL of dsRNA or ssDNA (21-mer) is applied. In certain embodiments, a composition of about 0.5 to about 1.5 mg/mL of a long dsRNA polynucleotide (i.e., about 50 to about 200 or more nucleotides) is applied. In certain embodiments, about 1 nmol to about 5 nmol of a dsRNA is applied to a plant. In certain embodiments, the polynucleotide composition as topically applied to the plant contains the at least one polynucleotide at a concentration of about 0.01 to about 10 milligrams per milliliter, or about 0.05 to about 2 milligrams per milliliter, or about 0.1 to about 2 milligrams per milliliter. Very large plants, trees, or vines may require correspondingly larger amounts of polynucleotides. When using long dsRNA molecules that can be processed into multiple oligonucleotides, lower concentrations can be used. To illustrate embodiments of the invention, the factor 1×, when applied to oligonucleotide molecules is arbitrarily used to denote a treatment of 0.8 nmol of polynucleotide molecule per plant; 10×, 8 nmol of polynucleotide molecule per plant; and 100×, 80 nmol of polynucleotide molecule per plant.

The polynucleotide compositions of this invention are useful in compositions, such as liquids that comprise polynucleotide molecules, alone or in combination with other components either in the same liquid or in separately applied liquids that provide a transfer agent. As used herein, a transfer agent is an agent that, when combined with a polynucleotide in a composition that is topically applied to a target plant surface, enables the polynucleotide to enter a plant cell. In certain embodiments, a transfer agent is an agent that conditions the surface of plant tissue, e.g., seeds, leaves, stems, roots, flowers, or fruits, to permeation by the polynucleotide molecules into plant cells. The transfer of polynucleotides into plant cells can be facilitated by the prior or contemporaneous application of a polynucleotide-transferring agent to the plant tissue. In some embodiments the transferring agent is applied subsequent to the application of the polynucleotide composition. The polynucleotide transfer agent enables a pathway for polynucleotides through cuticle wax barriers, stomata and/or cell wall or membrane barriers into plant cells. Suitable transfer agents to facilitate transfer of the polynucleotide into a plant cell include agents that increase permeability of the exterior of the plant or that increase permeability of plant cells to oligonucleotides or polynucleotides. Such agents to facilitate transfer of the composition into a plant cell include a chemical agent, or a physical agent, or combinations thereof. Chemical agents for conditioning or transfer include (a) surfactants, (b) an organic solvent or an aqueous solution or aqueous mixtures of organic solvents, (c) oxidizing agents, (d) acids, (e) bases, (f) oils, (g) enzymes, or combinations thereof. Embodiments of the method can optionally include an incubation step, a neutralization step (e.g., to neutralize an acid, base, or oxidizing agent, or to inactivate an enzyme), a rinsing step, or combinations thereof. Embodiments of agents or treatments for conditioning of a plant to permeation by polynucleotides include emulsions, reverse emulsions, liposomes, and other micellar-like compositions. Embodiments of agents or treatments for conditioning of a plant to permeation by polynucleotides include counter-ions or other molecules that are known to associate with nucleic acid molecules, e.g., inorganic ammonium ions, alkyl ammonium ions, lithium ions, polyamines such as spermine, spermidine, or putrescine, and other cations. Organic solvents useful in conditioning a plant to permeation by polynucleotides include DMSO, DMF, pyridine, N-pyrrolidine, hexamethylphosphoramide, acetonitrile, dioxane, polypropylene glycol, other solvents miscible with water or that will dissolve phosphonucleotides in non-aqueous systems (such as is used in synthetic reactions). Naturally derived or synthetic oils with or without surfactants or emulsifiers can be used, e.g., plant-sourced oils, crop oils (such as those listed in the 9th Compendium of Herbicide Adjuvants, publicly available on the worldwide web (internet) at herbicide.adjuvants.com can be used, e.g., paraffinic oils, polyol fatty acid esters, or oils with short-chain molecules modified with amides or polyamines such as polyethyleneimine or N-pyrrolidine. Transfer agents include, but are not limited to, organosilicone preparations.

In certain embodiments, an organosilicone preparation that is commercially available as Silwet® L-77 surfactant having CAS Number 27306-78-1 and EPA Number: CAL.REG.NO. 5905-50073-AA, and currently available from Momentive Performance Materials, Albany, N.Y. can be used to prepare a polynucleotide composition. In certain embodiments where a Silwet L-77 organosilicone preparation is used as a pre-spray treatment of plant leaves or other plant surfaces, freshly made concentrations in the range of about 0.015 to about 2 percent by weight (wt percent) (e.g., about 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.5 wt percent) are efficacious in preparing a leaf or other plant surface for transfer of polynucleotide molecules into plant cells from a topical application on the surface. In certain embodiments of the methods and compositions provided herein, a composition that comprises a polynucleotide molecule and an organosilicone preparation comprising Silwet L-77 in the range of about 0.015 to about 2 percent by weight (wt percent) (e.g., about 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.5 wt percent) is used or provided. In certain embodiments of the methods and compositions provided herein, a composition that comprises a polynucleotide molecule and an organosilicone preparation comprising Silwet L-77 in the range of about 0.3 to about 1 percent by weight (wt percent) or about 0.5 to about 1%. by weight (wt percent) is used or provided.

In certain embodiments of the methods and compositions provided herein, a composition that comprises a polynucleotide molecule and an organosilicone preparation comprising Silwet L-77 in the range of about 0.3 to about 1 percent by weight (wt percent) or about 0.5 to about 1%. by weight (wt percent) is used or provided. In certain embodiments, any of the commercially available organosilicone preparations provided in the following Table 1 can be used as transfer agents in a polynucleotide composition. In certain embodiments where an organosilicone preparation of the Table is used as a pre-spray treatment of plant leaves or other surfaces, freshly made concentrations in the range of about 0.015 to about 2 percent by weight (wt percent) (e.g., about 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.5 wt percent) are efficacious in preparing a leaf or other plant surface for transfer of polynucleotide molecules into plant cells from a topical application on the surface. In certain embodiments of the methods and compositions provided herein, a composition that comprises a polynucleotide molecule and an organosilicone preparation of Table 1 in the range of about 0.015 to about 2 percent by weight (wt percent) (e.g., about 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.5 (wt percent) is used or provided.

TABLE 1

Exemplary organosilicone preparations

| Name | CAS number | Manufacturer[1,2] |
|---|---|---|
| BREAK-THRU ® S 321 | na | Evonik Industries AG |
| BREAK-THRU ® S 200 | 67674-67-3 | Evonik Industries AG |
| BREAK-THRU ® OE 441 | 68937-55-3 | Evonik Industries AG |
| BREAK-THRU ® S 278 | 27306-78-1 | Evonik Goldschmidt |
| BREAK-THRU ® S 243 | na | Evonik Industries AG |
| Silwet ® L-77 | 27306-78-1 | Momentive Performance Materials |
| Silwet ® HS 429 | na | Momentive Performance Materials |
| Silwet ® HS 312 | na | Momentive Performance Materials |
| BREAK-THRU ® S 233 | 134180-76-0 | Evonik Industries AG |
| Silwet ® HS 508 | | Momentive Performance Materials |
| Silwet ® HS 604 | | Momentive Performance Materials |

[1]Evonik Industries AG, Essen, Germany
[2]Momentive Performance Materials, Albany, New York Organosilicone preparations used in the methods and compositions provided herein can comprise one or more effective organosilicone compounds. As used herein, the phrase "effective organosilicone compound" is used to describe any organosilicone compound that is found in an organosilicone preparation that enables a polynucleotide to enter a plant cell. In certain embodiments, an effective organosilicone compound can enable a polynucleotide to enter a plant cell in a manner permitting a polynucleotide mediated suppression of target gene expression in the plant cell. In general, effective organosilicone compounds include, but are not limited to, compounds that can comprise: i) a trisiloxane head group that is covalently linked to, ii) an alkyl linker including, but not limited to, an n-propyl linker, that is covalently linked to, iii) a poly glycol chain, that is covalently linked to, iv) a terminal group. Trisiloxane head groups of such effective organosilicone compounds include, but are not limited to, heptamethyltrisiloxane. Alkyl linkers can include, but are not limited to, an n-propyl linker. Poly glycol chains include, but are not limited to, polyethylene glycol or polypropylene glycol. Poly glycol chains can comprise a mixture that provides an average chain length "n" of about "7.5". In certain embodiments, the average chain length "n" can vary from about 5 to about 14. Terminal groups can include, but are not limited to, alkyl groups such as a methyl group. Effective organosilicone compounds are believed to include, but are not limited to, trisiloxane ethoxylate surfactants or polyalkylene oxide modified heptamethyl trisiloxane.

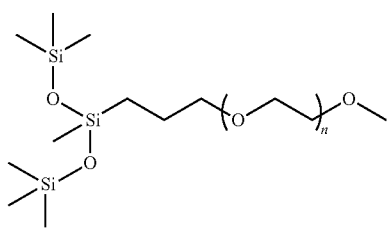

(Compound I: polyalkyleneoxide heptamethyltrisiloxane, average n=7.5).

One organosilicone compound believed to be ineffective comprises the formula:

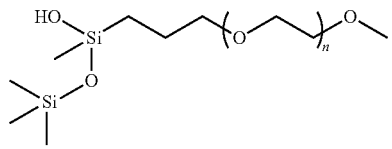

In certain embodiments, an organosilicone preparation that comprises an organosilicone compound comprising a trisiloxane head group is used in the methods and compositions provided herein. In certain embodiments, an organosilicone preparation that comprises an organosilicone compound comprising a heptamethyltrisiloxane head group is used in the methods and compositions provided herein. In certain embodiments, an organosilicone composition that comprises Compound I is used in the methods and compositions provided herein. In certain embodiments, an organosilicone composition that comprises Compound I is used in the methods and compositions provided herein. In certain embodiments of the methods and compositions provided herein, a composition that comprises a polynucleotide molecule and one or more effective organosilicone compound in the range of about 0.015 to about 2 percent by weight (wt percent) (e.g., about 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.5 wt percent) is used or provided.

In certain embodiments, the polynucleotide compositions that comprise an organosilicone preparation can comprise a salt such as ammonium chloride, tetrabutylphosphonium bromide, and/or ammonium sulfate. Ammonium chloride, tetrabutylphosphonium bromide, and/or ammonium sulfate can be provided in the polynucleotide composition at a concentration of about 0.5% to about 5% (w/v). An ammonium chloride, tetrabutylphosphonium bromide, and/or ammonium sulfate concentration of about 1% to about 3%, or about 2% (w/v) can also be used in the polynucleotide compositions that comprise an organosilicone preparation. In certain embodiments, the polynucleotide compositions can comprise an ammonium salt at a concentration greater or equal to 300 millimolar. In certain embodiments, the polynucleotide compositions that comprise an organosilicone preparation can comprise ammonium sulfate at concentrations from about 80 to about 1200 mM or about 150 mM to about 600 mM.

In certain embodiments, the polynucleotide compositions can also comprise a phosphate salt. Phosphate salts used in the compositions include, but are not limited to, calcium, magnesium, potassium, or sodium phosphate salts. In certain embodiments, the polynucleotide compositions can comprise a phosphate salt at a concentration of at least about 5 millimolar, at least about 10 millimolar, or at least about 20 millimolar. In certain embodiments, the polynucleotide compositions will comprise a phosphate salt in a range of about 1 mM to about 25 mM or in a range of about 5 mM to about 25 mM. In certain embodiments, the polynucleotide compositions can comprise sodium phosphate at a concentration of at least about 5 millimolar, at least about 10 millimolar, or at least about 20 millimolar. In certain embodiments, the polynucleotide compositions can comprise sodium phosphate at a concentration of about 5 millimolar, about 10 millimolar, or about 20 millimolar. In certain embodiments, the polynucleotide compositions will comprise a sodium phosphate salt in a range of about 1 mM to about 25 mM or in a range of about 5 mM to about 25 mM. In certain embodiments, the polynucleotide compositions will comprise a sodium phosphate salt in a range of about 10 mM to about 160 mM or in a range of about 20 mM to about 40 mM. In certain embodiments, the polynucleotide compositions can comprise a sodium phosphate buffer at a pH of about 6.8.

In certain embodiments, other useful transfer agents or adjuvants to transfer agents that can be used in polynucleotide compositions provided herein include surfactants and/or effective molecules contained therein. Surfactants and/or effective molecules contained therein include, but are not limited to, sodium or lithium salts of fatty acids (such as tallow or tallowamines or phospholipids) and organosilicone surfactants. In certain embodiments, the polynucleotide compositions that comprise a transfer agent are formulated with counter-ions or other molecules that are known to associate with nucleic acid molecules. Illustrative examples include tetraalkyl ammonium ions, trialkyl ammonium ions, sulfonium ions, lithium ions, and polyamines such as spermine, spermidine, or putrescine. In certain embodiments, the polynucleotide compositions are formulated with a non-polynucleotide herbicide. Non-polynucleotide herbicidal molecules include, but are not limited to, glyphosate, auxin-like benzoic acid herbicides including dicamba, chloramben, and TBA, glufosinate, auxin-like herbicides including phenoxy carboxylic acid herbicide, pyridine carboxylic acid herbicide, quinoline carboxylic acid herbicide, pyrimidine carboxylic acid herbicide, and benazolin-ethyl herbicide, sulfonylureas, imidazolinones, bromoxynil, delapon, cyclohezanedione, protoporphyrinogen oxidase inhibitors, and 4-hydroxyphenyl-pyruvate-dioxygenase inhibiting herbicides.

In certain embodiments, the polynucleotides used in the compositions that are essentially identical or essentially complementary to the target gene or transcript will comprise the predominant nucleic acid in the composition. Thus in certain embodiments, the polynucleotides that are essentially identical or essentially complementary to the target gene or transcript will comprise at least about 50%, 75%, 95%, 98%, or 100% of the nucleic acids provided in the composition by either mass or molar concentration. However, in certain embodiments, the polynucleotides that are essentially identical or essentially complementary to the target gene or transcript can comprise at least about 1% to about 50%, about 10% to about 50%, about 20% to about 50%, or about 30% to about 50% of the nucleic acids provided in the composition by either mass or molar concentration. Also provided are compositions where the polynucleotides that are essentially identical or essentially complementary to the target gene or transcript can comprise at least about 1% to 100%, about 10% to 100%, about 20% to about 100%, about 30% to about 50%, or about 50% to 100% of the nucleic acids provided in the composition by either mass or molar concentration.

Polynucleotides comprising ssDNA, dsDNA, ssRNA, dsRNA, or RNA/DNA hybrids that are essentially identical or complementary to certain plant target genes or transcripts and that can be used in compositions containing transfer agents that include, but are not limited to, organosilicone preparations, to suppress those target genes when topically applied to plants are disclosed in co-assigned U.S. patent application Ser. No. 13/042,856. Various polynucleotide herbicidal molecules, compositions comprising those polynucleotide herbicidal molecules and transfer agents that include, but are not limited to, organosilicone preparations, and methods whereby herbicidal effects are obtained by the topical application of such compositions to plants are also disclosed in co-assigned U.S. patent application Ser. No. 13/042,856, and those polynucleotide herbicidal molecules, compositions, and methods are incorporated herein by reference in their entireties. Genes encoding proteins that can provide tolerance to an herbicide and/or that are targets of a herbicide are collectively referred to herein as "herbicide target genes". Herbicide target genes include, but are not limited to, a 5-enolpyruvylshikimate-3-phosphate synthase (EPSPS), a glyphosate oxidoreductase (GOX), a glyphosate decarboxylase, a glyphosate-N-acetyl transferase (GAT), a dicamba monooxygenase, a phosphinothricin acetyltransferase, a 2,2-dichloropropionic acid dehalogenase, an acetohydroxyacid synthase, an acetolactate synthase, a haloarylnitrilase, an acetyl-coenzyme A carboxylase (ACCase), a dihydropteroate synthase, a phytoene desaturase (PDS), a protoporphyrin IX oxygenase (PPO), a hydroxyphenylpyruvate dioxygenase (HPPD), a para-aminobenzoate synthase, a glutamine synthase, a cellulose synthase, a beta tubulin, and a serine hydroxymethyltransferase gene. The effects of applying certain compositions comprising polynucleotides that are essentially identical or complementary to certain herbicide target genes and transfer agents on plants containing the herbicide target genes was shown to be potentiated or enhanced by subsequent application of an herbicide that targets the same gene as the polynucleotide in co-assigned U.S. patent application Ser. No. 13/042,856. For example, compositions comprising polynucleotides targeting the EPSPS herbicide target gene were potentiated by glyphosate in experiments disclosed in co-assigned U.S. patent application Ser. No. 13/042,856.

In certain embodiments of the compositions and methods disclosed herein, the composition comprising a polynucleotide and a transfer agent can thus further comprise a second polynucleotide comprising at least 19 contiguous nucleotides that are essentially identical or essentially complementary to a transcript to a protein that confers resistance to a herbicide. In certain embodiments, the second polynucleotide does not comprise a polynucleotide that is essentially identical or essentially complementary to a transcript encoding a protein of a target plant that confers resistance to said herbicidal molecule. Thus, in an exemplary and non-limiting embodiment, the second polynucleotide could be essentially identical or essentially complementary to a transcript encoding a protein that confers resistance to a herbicide in a weed (such as an EPSPS encoding transcript) but would not be essentially identical or essentially complementary to a transcript encoding a protein that confers resistance to that same herbicide in a crop plant.

In certain embodiments, the polynucleotide compositions that comprise a transfer agent can comprise glycerin. Glycerin can be provided in the composition at a concentration of about 0.1% to about 1% (w/v or v/v). A glycerin concentration of about 0.4% to about 0.6%, or about 0.5% (w/v or v/v) can also be used in the polynucleotide compositions that comprise a transfer agent.

In certain embodiments, the polynucleotide compositions that comprise a transfer agent can further comprise organic solvents. Such organic solvents include, but are not limited to, DMSO, DMF, pyridine, N-pyrrolidine, hexamethylphosphoramide, acetonitrile, dioxane, polypropylene glycol, other solvents miscible with water or that will dissolve phosphonucleotides in non-aqueous systems (such as is used in synthetic reactions).

In certain embodiments, the polynucleotide compositions that comprise a transfer agent can further comprise naturally derived or synthetic oils with or without surfactants or emulsifiers. Such oils include, but are not limited to, plant-sourced oils, crop oils (such as those listed in the 9th Compendium of Herbicide Adjuvants, publicly available on line at herbicide.adjuvants.com), paraffinic oils, polyol fatty acid esters, or oils with short-chain molecules modified with amides or polyamines such as polyethyleneimine or N-pyrrolidine.

In aspects of the invention, methods include one or more applications of the composition comprising a polynucleotide and a transfer agent or one or more effective components contained therein. In certain embodiments of the methods, one or more applications of a transfer agent or one or more effective components contained therein can precede one or more applications of the composition comprising a polynucleotide and a transfer agent. In embodiments where a transfer agent and/or one or more effective molecules contained therein is used either by itself as a pre-treatment or as part of a composition that includes a polynucleotide, embodiments of the polynucleotide molecules are double-stranded RNA oligonucleotides, single-stranded RNA oligonucleotides, double-stranded RNA polynucleotides, single-stranded RNA polynucleotides, double-stranded DNA oligonucleotides, single-stranded DNA oligonucleotides, double-stranded DNA polynucleotides, single-stranded DNA polynucleotides, chemically modified RNA or DNA oligonucleotides or polynucleotides or mixtures thereof.

Compositions and methods of the invention are useful for modulating or suppressing the expression of an endogenous target gene or transgenic target gene in a plant cell or plant. In certain embodiments of the methods and compositions provided herein, expression of Polyphenol oxidase (PPO) target genes can be suppressed completely, partially and/or transiently to result in improved shelf life and reduced postharvest losses. In various embodiments, a target gene includes coding (protein-coding or translatable) sequence, non-coding (non-translatable) sequence, or both coding and non-coding sequence. Compositions of the invention can include polynucleotides and oligonucleotides designed to target multiple genes, or multiple segments of one or more genes. The target gene can include multiple consecutive segments of a target gene, multiple non-consecutive segments of a target gene, multiple alleles of a target gene, or multiple target genes from one or more species. Examples of target genes of the present invention include endogenous Polyphenol oxidase (PPO) genes and Polyphenol oxidase (PPO) transgenes.

Target Polyphenol oxidase (PPO) genes and plants containing those target Polyphenol oxidase (PPO) genes can be obtained from: i) row crop plants including, but are not limited to, corn, soybean, cotton, canola, sugar beet, alfalfa, sugarcane, rice, and wheat; ii) vegetable plants including, but not limited to, tomato, potato, sweet pepper, hot pepper, melon, watermelon, cucumber, eggplant, cauliflower, broccoli, lettuce, spinach, onion, peas, carrots, sweet corn, Chinese cabbage, leek, fennel, pumpkin, squash or gourd, radish, Brussels sprouts, tomatillo, garden beans, dry beans, or okra; iii) culinary plants including, but not limited to, basil, parsley, coffee, or tea; iv) fruit plants including but not limited to apple, pear, cherry, peach, plum, apricot, banana, plantain, table grape, wine grape, citrus, avocado, mango, or berry; v) a tree grown for ornamental or commercial use, including, but not limited to, a fruit or nut tree; or, vi) an ornamental plant (e.g., an ornamental flowering plant or shrub or turf grass). The methods and compositions provided herein can also be applied to plants produced by a cutting, cloning, or grafting process (i.e., a plant not grown from a seed) including fruit trees and plants that include, but are not limited to, citrus, apples, avocados, tomatoes, eggplant, cucumber, melons, watermelons, and grapes as well as various ornamental plants. Such row crop, vegetable, culinary, fruit, tree, or ornamental plants exhibiting improvements that result from suppressing expression of Polyphenol oxidase (PPO) gene are provided herein. Such row crop, vegetable, culinary, fruit, tree, or ornamental plant parts or processed plant products exhibiting improved shelf life and reduced postharvest losses that result from suppressing expression of Polyphenol oxidase (PPO) gene are also provided herein. Such plant parts can include, but are not limited to, flowers, stems, tubers, fruit, anthers, meristems, ovules, pollen, leaves, or seeds. Such processed plant products obtained from the plant parts can include, but are not limited to, a meal, a pulp, a feed, or a food product.

An aspect of the invention provides a method for modulating expression of a Polyphenol oxidase (PPO) gene in a plant including (a) conditioning of a plant to permeation by polynucleotides and (b) treatment of the plant with the polynucleotide molecules, wherein the polynucleotide molecules include at least one segment of 18 or more contiguous nucleotides cloned from or otherwise identified from the target Polyphenol oxidase (PPO) gene in either anti-sense or sense orientation, whereby the polynucleotide molecules permeate the interior of the plant and induce modulation of the target Polyphenol oxidase (PPO) gene. The conditioning and polynucleotide application can be performed separately or in a single step. When the conditioning and polynucleotide application are performed in separate steps, the conditioning can precede or can follow the polynucleotide application within minutes, hours, or days. In some embodiments more than one conditioning step or more than one polynucleotide molecule application can be performed on the same plant. In embodiments of the method, the segment can be cloned or identified from (a) coding (protein-encoding), (b) non-coding (promoter and other gene related molecules), or (c) both coding and non-coding parts of the target Polyphenol oxidase (PPO) gene. Non-coding parts include DNA, such as promoter regions or the RNA transcribed by the DNA that provide RNA regulatory molecules, including but not limited to: introns, 5' or 3' untranslated regions, and microRNAs (miRNA), trans-acting siRNAs, natural anti-sense siRNAs, and other small RNAs with regulatory function or RNAs having structural or enzymatic function including but not limited to: ribozymes, ribosomal RNAs, t-RNAs, aptamers, and riboswitches. In certain embodiments where the polynucleotide used in the composition comprises a promoter sequence essentially identical to, or essentially complementary to at least 18 contiguous nucleotides of the promoter of the endogenous target Polyphenol oxidase (PPO) gene, the promoter sequence of the polynucleotide is not operably linked to another sequence that is transcribed from the promoter sequence.

Compositions comprising a polynucleotide and a transfer agent provided herein can be topically applied to a plant or plant part by any convenient method, e.g., spraying or coating with a powder, or with a liquid composition comprising any of an emulsion, suspension, or solution. Such topically applied sprays or coatings can be of either all or of any a portion of the surface of the plant or plant part. Similarly, the compositions comprising a transfer agent or other pre-treatment can in certain embodiments be applied to the plant or plant part by any convenient method, e.g., spraying or wiping a solution, emulsion, or suspension. Compositions comprising a polynucleotide and a transfer agent provided herein can be topically applied to plant parts that include, but are not limited to, flowers, stems, tubers, meristems, ovules, fruit, anthers, pollen, leaves, roots, or seeds.

Application of compositions comprising a polynucleotide and a transfer agent to seeds is specifically provided herein. Seeds can be contacted with such compositions by spraying, misting, immersion, and the like.

In certain embodiments, application of compositions comprising a polynucleotide and a transfer agent to plants, plant parts, or seeds in particular can provide for the improved shelf life and reduced postharvest losses in progeny plants, plant parts, or seeds derived from those treated plants, plant parts, or seeds. In certain embodiments, progeny plants, plant parts, or seeds derived from those treated plants, plant parts, or seeds will exhibit improved shelf life and reduced postharvest losses that result from suppressing expression of Polyphenol oxidase (PPO) gene. In certain embodiments, the methods and compositions provided herein can provide for improved shelf life and reduced postharvest losses in progeny plants or seeds as a result of epigenetically inherited suppression of Polyphenol oxidase (PPO) gene expression. In certain embodiments, such progeny plants exhibit improved shelf life and reduced postharvest losses from epigenetically inherited suppression of Polyphenol oxidase (PPO) gene expression that is not caused by a transgene where the polynucleotide is operably linked to a promoter, a viral vector, or a copy of the polynucleotide that is integrated into a non-native location in the chromosomal DNA of the plant. Without seeking to be limited by theory, progeny plants or seeds derived from those treated plants, plant parts, or seeds can exhibit an improvement in improved shelf life and reduced postharvest losses through an epigenetic mechanism that provides for propagation of an epigenetic condition where suppression of Polyphenol oxidase (PPO) gene expression occurs in the progeny plants, plant parts, or plant seeds. In certain embodiments, progeny plants or seeds exhibiting improved shelf life and reduced postharvest losses as a result of epigenetically inherited suppression of Polyphenol oxidase (PPO) gene expression can also exhibit increased methylation, and in particular, increased methylation of cytosine residues, in the endogenous Polyphenol oxidase (PPO) gene of the plant. Plant parts, including seeds, of the progeny plants that exhibit improved shelf life and reduced postharvest losses as a result of epigenetically inherited suppression of Polyphenol oxidase (PPO) gene expression, can also in certain embodiments exhibit increased methylation, and in particular, increased methylation of cytosine residues, in the endogenous Polyphenol oxidase (PPO) gene. In certain embodiments, DNA methylation levels in DNA encoding the endogenous Polyphenol oxidase (PPO) gene can be compared in plants that exhibit the improved shelf life and reduced postharvest losses and control plants that do not exhibit the improved shelf life and reduced postharvest losses to correlate the presence of the improved shelf life and reduced postharvest losses to epigenetically inherited suppression of Polyphenol oxidase (PPO) gene expression and to identify plants that comprise the epigenetically inherited improved shelf life and reduced postharvest losses.

Various methods of spraying compositions on plants or plant parts can be used to topically apply to a plant surface a composition comprising a polynucleotide that comprises a transfer agent. In the field, a composition can be applied with a boom that extends over the crops and delivers the composition to the surface of the plants or with a boomless sprayer that distributes a composition across a wide area. Agricultural sprayers adapted for directional, broadcast, or banded spraying can also be used in certain embodiments. Sprayers adapted for spraying particular parts of plants including, but not limited to, leaves, the undersides of leaves, flowers, stems, male reproductive organs such as tassels, meristems, pollen, ovules, and the like can also be used. Compositions can also be delivered aerially, such as by a crop dusting airplane. In certain embodiments, the spray can be delivered with a pressurized backpack sprayer calibrated to deliver the appropriate rate of the composition. In certain embodiments, such a backpack sprayer is a carbon dioxide pressurized sprayer with a 11015 flat fan or equivalent spray nozzle with a customized single nozzle assembly (to minimize waste) at a spray pressure of about 0.25 MPa and/or any single nozzle sprayer providing an effective spray swath of 60 cm above the canopy of 3 to 12 inch tall growing plants can be used. Plants in a greenhouse or growth chamber can be treated using a track sprayer or laboratory sprayer with a 11001XR or equivalent spray nozzle to deliver the sample solution at a determined rate. An exemplary and non-limiting rate is about 140 L/ha at about 0.25 MPa pressure.

In certain embodiments, it is also contemplated that a plant part can be sprayed with the composition comprising a polynucleotide that comprises a transfer agent. Such plant parts can be sprayed either pre- or post-harvest to provide improved shelf life and reduced postharvest losses in the plant part that results from suppression of Polyphenol oxidase (PPO) gene expression. Compositions can be topically applied to plant parts attached to a plant by a spray as previously described. Compositions can be topically applied to plant parts that are detached from a plant by a spray as previously described or by an alternative method. Alternative methods for applying compositions to detached parts include, but are not limited to, passing the plant parts through a spray by a conveyor belt or trough, or immersing the plant parts in the composition.

Compositions comprising polynucleotides and transfer agents can be applied to plants or plant parts at one or more developmental stages as desired and/or as needed. Application of compositions to pre-germination seeds and/or to post-germination seedlings is provided in certain embodiments. Seeds can be treated with polynucleotide compositions provided herein by methods including, but not limited to, spraying, immersion, or any process that provides for coating, imbibition, and/or uptake of the polynucleotide composition by the seed. Seeds can be treated with polynucleotide compositions using seed batch treatment systems or continuous flow treatment systems. Seed coating systems are at least described in U.S. Pat. Nos. 6,582,516, 5,891,246, 4,079,696, and 4,023,525. Seed treatment can also be effected in laboratory or commercial scale treatment equipment such as a tumbler, a mixer, or a pan granulator. A polynucleotide composition used to treat seeds can contain one or more other desirable components including, but not limited to liquid diluents, binders to serve as a matrix for the polynucleotide, fillers for protecting the seeds during stress conditions, and plasticizers to improve flexibility, adhesion and/or spreadability of the coating. In addition, for oily polynucleotide compositions containing little or no filler, drying agents such as calcium carbonate, kaolin or bentonite clay, perlite, diatomaceous earth or any other adsorbent material can be added. Use of such components in seed treatments is described in U.S. Pat. No. 5,876,739. Additional ingredients can be incorporated into the polynucleotide compositions used in seed treatments. Such ingredients include but are not limited to: conventional sticking agents, dispersing agents such as methylcellulose (Methocel A15LV or Methocel A15C, for example, serve as combined dispersant/sticking agents for use in seed treatments), polyvinyl alcohol (e.g., Elvanol 51-05), lecithin (e.g., Yelkinol P), polymeric dispersants (e.g., polyvinylpyrrolidone/vinyl acetate PVPNA S-630), thickeners (e.g., clay thickeners such as Van Gel B to improve viscosity and reduce settling of particle suspensions), emulsion stabilizers, surfactants, antifreeze compounds (e.g., urea), dyes, colorants, and the like that can be combined with compositions comprising a polynucleotide and a transfer agent. Further ingredients used in compositions that can be applied to seeds can be found in McCutcheon's, vol. 1, "Emulsifiers and Detergents," MC Publishing Company, Glen Rock, N.J., U.S.A., 1996 and in McCutcheon's, vol. 2, "Functional Materials," MC Publishing Company, Glen Rock, N.J., U.S.A., 1996. Methods of applying compositions to seeds and pesticidal compositions that can be used to treat seeds are described in U.S. Patent Application Publication No. 20080092256, which is incorporated herein by reference in its entirety.

Application of the compositions in early, mid-, and late vegetative stages of plant development is provided in certain embodiments. Application of the compositions in early, mid, and late reproductive stages is also provided in certain embodiments. Application of the compositions to plant parts at different stages of maturation is also provided.

In certain embodiments, methods and polynucleotide compositions are provided that can be applied to living plant cells/tissues to suppress expression of a Polyphenol oxidase 11 (PPO11) gene and that provide improved shelf life, reduced browning, reduced postharvest losses or combinations thereof to a crop plant in need of the benefit. Also provided herein are plants and plant parts exhibiting improved shelf life and reduced postharvest losses as well as processed products of such plants or plant parts. In certain embodiments, the compositions may be topically applied to the surface of a plant, such as to the surface of a leaf, tuber, or fruit, and the compositions may include a transfer agent. Aspects of the method can be applied to various crops, for example, including but not limited to lettuce, apples and potatoes. The methods and compositions provided herein can also be applied to plants produced by a cutting, cloning, or grafting process (i.e., a plant not grown from a seed) that include fruit trees and plants. Fruit trees produced by such processes include, but are not limited to, citrus and apple trees. Plants produced by such processes include, but are not limited to, avocados, tomatoes, eggplant, cucumber, melons, watermelons, and grapes as well as various ornamental plants.

Without being bound by theory, in certain embodiments, the compositions and methods of the present invention are believed to operate through one or more of the several natural cellular pathways involved in RNA-mediated gene suppression as generally described in Brodersen and Voinnet (2006), Trends Genetics, 22:268-280; Tomari and Zamore (2005) Genes & Dev., 19:517-529; Vaucheret (2006) Genes Dev., 20:759-771; Meins et al. (2005) Annu. Rev. Cell Dev. Biol., 21:297-318; and Jones-Rhoades et al. (2006) Annu. Rev. Plant Biol., 57:19-53. RNA-mediated gene suppression generally involves a double-stranded RNA (dsRNA) intermediate that is formed intra-molecularly within a single RNA molecule or inter-molecularly between two RNA molecules. This longer dsRNA intermediate is processed by a ribonuclease of the RNAase III family (Dicer or Dicer-like ribonuclease) to one or more shorter double-stranded RNAs, one strand of which is incorporated into the RNA-induced silencing complex ("RISC"). For example, the siRNA pathway involves the cleavage of a longer double-stranded RNA intermediate to small interfering RNAs ("siRNAs"). The size of siRNAs is believed to range from about 19 to about 25 base pairs, but the most common classes of siRNAs in plants include those containing 21 to 24 base pairs (See, Hamilton et al. (2002) EMBO J., 21:4671-4679).

Plant Transformation Constructs

Vectors used for plant transformation may include, for example, plasmids, cosmids, YACs (yeast artificial chromosomes), BACs (bacterial artificial chromosomes) or any other suitable cloning system, as well as fragments of DNA therefrom. Thus when the term "vector" or "expression vector" is used, all of the foregoing types of vectors, as well as nucleic acid sequences isolated therefrom, are included. It is contemplated that utilization of cloning systems with large insert capacities will allow introduction of large DNA sequences comprising more than one selected gene. In accordance with the invention, this could be used to introduce genes corresponding to an entire biosynthetic pathway into a plant. Introduction of such sequences may be facilitated by use of bacterial or yeast artificial chromosomes (BACs or YACs, respectively), or even plant artificial chromosomes. For example, the use of BACs for *Agrobacterium*-mediated transformation was disclosed by Hamilton et al., *Proc. Natl. Acad. Sci. USA*, 93(18):9975-9979, 1996.

Particularly useful for transformation are expression cassettes which have been isolated from such vectors. DNA segments used for transforming plant cells will, of course, generally comprise the cDNA, gene or genes which one desires to introduce into and have expressed in the host cells. These DNA segments can further include structures such as promoters, enhancers, polylinkers, or even regulatory genes as desired. The DNA segment or gene chosen for cellular introduction will often encode a protein which will be expressed in the resultant recombinant cells resulting in a screenable or selectable trait and/or which will impart an improved phenotype to the resulting transgenic plant. However, this may not always be the case, and the present invention also encompasses transgenic plants incorporating non-expressed transgenes. Preferred components likely to be included with vectors used in the current invention are as follows.

A. Regulatory Elements

Exemplary promoters for expression of a nucleic acid sequence include plant promoter such as the CaMV 35S promoter (Odell et al., 1985), or others such as CaMV 19S (Lawton et al., 1987), nos (Ebert et al., 1987), Adh (Walker et al., 1987), sucrose synthase (Yang and Russell, 1990), a tubulin, actin (Wang et al., 1992), cab (Sullivan et al., 1989), PEPCase (Hudspeth and Grula, 1989) or those associated with the R gene complex (Chandler et al., 1989). Tissue specific promoters such as root cell promoters (Conkling et al., 1990) and tissue specific enhancers (Fromm et al., 1986) are also contemplated to be useful, as are inducible promoters such as ABA- and turgor-inducible promoters. The PAL2 promoter may in particular be useful with the invention (U.S. Pat. Appl. Pub. 2004/0049802, the entire disclosure of which is specifically incorporated herein by reference).

The DNA sequence between the transcription initiation site and the start of the coding sequence, i.e., the untranslated leader sequence, can also influence gene expression. One may thus wish to employ a particular leader sequence with a transformation construct of the invention. Preferred leader sequences are contemplated to include those which comprise sequences predicted to direct optimum expression of the attached gene, i.e., to include a preferred consensus leader sequence which may increase or maintain mRNA stability and prevent inappropriate initiation of translation.

The choice of such sequences will be known to those of skill in the art in light of the present disclosure. Sequences that are derived from genes that are highly expressed in plants will typically be preferred.

It is contemplated that vectors for use in accordance with the present invention may be constructed to include an ocs enhancer element. This element was first identified as a 16 bp palindromic enhancer from the octopine synthase (ocs) gene of *Agrobacterium* (Ellis et al., 1987), and is present in at least 10 other promoters (Bouchez et al., 1989). The use of an enhancer element, such as the ocs element and particularly multiple copies of the element, may act to increase the level of transcription from adjacent promoters when applied in the context of plant transformation.

It is envisioned that polynucleotide sequences or selected DNA sequences may be introduced under the control of novel promoters or enhancers, etc., or homologous or tissue specific promoters or control elements. Vectors for use in tissue-specific targeting of genes in transgenic plants will typically include tissue-specific promoters and may also include other tissue-specific control elements such as enhancer sequences. Promoters which direct specific or enhanced expression in certain plant tissues will be known to those of skill in the art in light of the present disclosure. These include, for example, the rbcS promoter, specific for green tissue; the ocs, nos and mas promoters which have higher activity in roots or wounded leaf tissue. In certain embodiments, promoters can be employed that cause low expression of the selected DNA. Low expression promoters can be obtained by mutation and/or recombination of DNA elements of promoters that cause high expression or by selecting upstream regulatory elements of genes that cause expression of mRNA or protein with low abundance.

B. Terminators

Transformation constructs prepared in accordance with the invention will typically include a 3' end DNA sequence that acts as a signal to terminate transcription and allow for the poly-adenylation of the mRNA produced by coding sequences operably linked to a promoter. Examples of terminators that are deemed to be useful in this context include those from the nopaline synthase gene of *Agrobacterium tumefaciens* (nos 3' end) (Bevan et al., 1983), the terminator for the T7 transcript from the octopine synthase gene of *Agrobacterium tumefaciens*, and the 3' end of the protease inhibitor I or II genes from potato or tomato. Regulatory elements such as an Adh intron (Callis et al., 1987), sucrose synthase intron (Vasil et al., 1989) or TMV omega element (Gallie et al., 1989), may further be included where desired.

C. Transit or Signal Peptides

Sequences that are joined to the coding sequence of an expressed gene, which are removed post-translationally from the initial translation product and which facilitate the transport of the protein into or through intracellular or extracellular membranes, are termed transit (usually into vacuoles, vesicles, plastids and other intracellular organelles) and signal sequences (usually to the endoplasmic reticulum, golgi apparatus and outside of the cellular membrane). By facilitating the transport of the protein into compartments inside and outside the cell, these sequences may increase the accumulation of gene product protecting them from proteolytic degradation. These sequences also allow for additional mRNA sequences from highly expressed genes to be attached to the coding sequence of the genes. Since mRNA being translated by ribosomes is more stable than naked mRNA, the presence of translatable mRNA in front of the gene may increase the overall stability of the mRNA transcript from the gene and thereby increase synthesis of the gene product. Since transit and signal sequences are usually post-translationally removed from the initial translation product, the use of these sequences allows for the addition of extra translated sequences that may not appear on the final polypeptide. It further is contemplated that targeting of certain proteins may be desirable in order to enhance the stability of the protein (U.S. Pat. No. 5,545,818, incorporated herein by reference in its entirety).

Additionally, vectors may be constructed and employed in the intracellular targeting of a specific gene product within the cells of a transgenic plant or in directing a protein to the extracellular environment. This generally will be achieved by joining a DNA sequence encoding a transit or signal peptide sequence to the coding sequence of a particular gene. The resultant transit, or signal, peptide will transport the protein to a particular intracellular, or extracellular destination, respectively, and will then be post-translationally removed.

D. Marker Genes

By employing a selectable or screenable marker protein, one can provide or enhance the ability to identify transformants. "Marker genes" are genes that impart a distinct phenotype to cells expressing the marker protein and thus allow such transformed cells to be distinguished from cells that do not have the marker. Such genes may encode either a selectable or screenable marker, depending on whether the marker confers a trait which one can "select" for by chemical means, i.e., through the use of a selective agent (e.g., a herbicide, antibiotic, or the like), or whether it is simply a trait that one can identify through observation or testing, i.e., by "screening" (e.g., the green fluorescent protein). Of course, many examples of suitable marker proteins are known to the art and can be employed in the practice of the invention.

Included within the terms selectable or screenable markers also are genes which encode a "secretable marker" whose secretion can be detected as a means of identifying or selecting for transformed cells. Examples include markers which are secretable antigens that can be identified by antibody interaction, or even secretable enzymes which can be detected by their catalytic activity. Secretable proteins fall into a number of classes, including small, diffusible proteins detectable, e.g., by ELISA; small active enzymes detectable in extracellular solution (e.g., alpha-amylase, beta-lactamase, phosphinothricin acetyltransferase); and proteins that are inserted or trapped in the cell wall (e.g., proteins that include a leader sequence such as that found in the expression unit of extensin or tobacco PR S).

Many selectable marker coding regions are known and could be used with the present invention including, but not limited to, neo (Potrykus et al., 1985), which provides kanamycin resistance and can be selected for using kanamycin, G418, paromomycin, etc.; bar, which confers bialaphos or phosphinothricin resistance; a mutant EPSP synthase protein (Hinchee et al., 1988) conferring glyphosate resistance; a nitrilase such as bxn from *Klebsiella ozaenae* which confers resistance to bromoxynil (Stalker et al., 1988); a mutant acetolactate synthase (ALS) which confers resistance to imidazolinone, sulfonylurea or other ALS inhibiting chemicals (European Patent Application 154, 204, 1985); a methotrexate resistant DHFR (Thillet et al., 1988), a dalapon dehalogenase that confers resistance to the herbicide dalapon; or a mutated anthranilate synthase that confers resistance to 5-methyl tryptophan.

An illustrative embodiment of selectable marker capable of being used in systems to select transformants are those that encode the enzyme phosphinothricin acetyltransferase, such as the bar gene from *Streptomyces hygroscopicus* or the pat gene from *Streptomyces viridochromogenes*. The enzyme phosphinothricin acetyl transferase (PAT) inactivates the active ingredient in the herbicide bialaphos, phosphinothricin (PPT). PPT inhibits glutamine synthetase, (Murakami et al., 1986; Twell et al., 1989) causing rapid accumulation of ammonia and cell death.

Screenable markers that may be employed include a beta-glucuronidase (GUS) or uidA gene which encodes an enzyme for which various chromogenic substrates are known; an R-locus gene, which encodes a product that regulates the production of anthocyanin pigments (red color) in plant tissues (Dellaporta et al., 1988); a beta-lactamase gene (Sutcliffe, 1978), which encodes an enzyme for which various chromogenic substrates are known (e.g., PADAC, a chromogenic cephalosporin); a xylE gene (Zukowsky et al., 1983) which encodes a catechol dioxygenase that can convert chromogenic catechols; an alpha-amylase gene (Ikuta et al., 1990); a tyrosinase gene (Katz et al., 1983) which encodes an enzyme capable of oxidizing tyrosine to DOPA and dopaquinone which in turn condenses to form the easily-detectable compound melanin; a beta-galactosidase gene, which encodes an enzyme for which there are chromogenic substrates; a luciferase (lux) gene (Ow et al., 1986), which allows for bioluminescence detection; an aequorin gene (Prasher et al., 1985) which may be employed in calcium-sensitive bioluminescence detection; or a gene encoding for green fluorescent protein (Sheen et al., 1995; Haseloff et al., 1997; Reichel et al., 1996; Tian et al., 1997; WO 97/41228). The gene that encodes green fluorescent protein (GFP) is also contemplated as a particularly useful reporter gene (Sheen et al., 1995; Haseloff et al., 1997; Reichel et al., 1996; Tian et al., 1997; WO 97/41228). Expression of green fluorescent protein may be visualized in a cell or plant as fluorescence following illumination by particular wavelengths of light.

Antisense and RNAi Constructs

Antisense and RNAi treatments represent one way of altering PPO11 activity in accordance with the invention. In particular, constructs comprising a PPO11 biosynthesis coding sequence, including fragments thereof, in antisense orientation, or combinations of sense and antisense orientation, may be used to decrease or effectively eliminate the expression of a PPO11 gene in a plant and obtain an improvement in shelf life as is described herein. Accordingly, this may be used to "knock-out" the PPO11 or homologous sequences thereof.

Techniques for RNAi are well known in the art and are described in, for example, Lehner et al., (2004) and Downward (2004). The technique is based on the fact that double stranded RNA is capable of directing the degradation of messenger RNA with sequence complementary to one or the other strand (Fire et al., 1998). Therefore, by expression of a particular coding sequence in sense and antisense orientation, either as a fragment or longer portion of the corresponding coding sequence, the expression of that coding sequence can be down-regulated.

Antisense, and in some aspects RNAi, methodology takes advantage of the fact that nucleic acids tend to pair with "complementary" sequences. By complementary, it is meant that polynucleotides are those which are capable of basepairing according to the standard Watson-Crick complementarity rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

Targeting double-stranded (ds) DNA with polynucleotides leads to triple-helix formation; targeting RNA will lead to double-helix formation. Antisense oligonucleotides, when introduced into a target cell, specifically bind to their target polynucleotide and interfere with transcription, RNA processing, transport, translation and/or stability. Antisense and RNAi constructs, or DNA encoding such RNA's, may be employed to inhibit gene transcription or translation or both within a host cell, either in vitro or in vivo, such as within a host plant cell. In certain embodiments of the invention, such an oligonucleotide may comprise any unique portion of a nucleic acid sequence provided herein. In certain embodiments of the invention, such a sequence comprises at least 18, 19, 20, 21, 22, 23, 24, 25, 26, 27, 28, 29, or 30 or more contiguous nucleic acids of the nucleic acid sequence of a PPO11 gene, and/or complements thereof, which may be in sense and/or antisense orientation. By including sequences in both sense and antisense orientation, increased suppression of the corresponding coding sequence may be achieved.

Constructs may be designed that are complementary to all or part of the promoter and other control regions, exons, introns or even exon-intron boundaries of a gene. It is contemplated that the most effective constructs will include regions complementary to intron/exon splice junctions. Thus, it is proposed that a preferred embodiment includes a construct with complementarity to regions within 50-200 bases of an intron-exon splice junction. It has been observed that some exon sequences can be included in the construct without seriously affecting the target selectivity thereof. The amount of exonic material included will vary depending on the particular exon and intron sequences used. One can readily test whether too much exon DNA is included simply by testing the constructs in vitro to determine whether normal cellular function is affected or whether the expression of related genes having complementary sequences is affected.

As stated above, "complementary" or "antisense" means polynucleotide sequences that are substantially complementary over their entire length and have very few base mismatches. For example, sequences of fifteen bases in length may be termed complementary when they have complementary nucleotides at thirteen or fourteen positions. Naturally, sequences which are completely complementary will be sequences which are entirely complementary throughout their entire length and have no base mismatches. Other sequences with lower degrees of homology also are contemplated. For example, an RNAi or antisense construct which has limited regions of high homology, but also contains a non-homologous region (e.g., ribozyme; see above) could be designed. These molecules, though having less than 50% homology, would bind to target sequences under appropriate conditions.

It may be advantageous to combine portions of genomic DNA with cDNA or synthetic sequences to generate specific constructs. For example, where an intron is desired in the ultimate construct, a genomic clone will need to be used. The cDNA or a synthesized polynucleotide may provide more convenient restriction sites for the remaining portion of the construct and, therefore, would be used for the rest of the sequence.

Methods for Genetic Transformation

Suitable methods for transformation of plant or other cells for use with the current invention are believed to include virtually any method by which DNA can be introduced into a cell, such as by direct delivery of DNA such as by PEG-mediated transformation of protoplasts (Omirulleh et al., 1993), by desiccation/inhibition-mediated DNA uptake (Potrykus et al., 1985), by electroporation (U.S. Pat. No. 5,384,253, specifically incorporated herein by reference in its entirety), by agitation with silicon carbide fibers (Kaeppler et al., 1990; U.S. Pat. No. 5,302,523, specifically incorporated herein by reference in its entirety; and U.S. Pat. No. 5,464,765, specifically incorporated herein by reference in its entirety), by Agrobacterium-mediated transformation (U.S. Pat. No. 5,591,616 and U.S. Pat. No. 5,563,055; both specifically incorporated herein by reference) and by acceleration of DNA coated particles (U.S. Pat. No. 5,550,318; U.S. Pat. No. 5,538,877; and U.S. Pat. No. 5,538,880; each specifically incorporated herein by reference in its entirety), etc. Through the application of techniques such as these, the cells of virtually any plant species may be stably transformed, and these cells developed into transgenic plants.

A. Agrobacterium-Mediated Transformation

Agrobacterium-mediated transfer is a widely applicable system for introducing genes into plant cells because the DNA can be introduced into whole plant tissues, thereby bypassing the need for regeneration of an intact plant from a protoplast. The use of Agrobacterium-mediated plant integrating vectors to introduce DNA into plant cells is well known in the art. See, for example, the methods described by Fraley et al., (1985), Rogers et al., (1987) and U.S. Pat. No. 5,563,055, specifically incorporated herein by reference in its entirety.

Agrobacterium-mediated transformation is most efficient in dicotyledonous plants and is the preferable method for transformation of dicots, including Arabidopsis, tobacco, tomato, alfalfa and potato. Indeed, while Agrobacterium-mediated transformation has been routinely used with dicotyledonous plants for a number of years, it has only recently become applicable to monocotyledonous plants. Advances in Agrobacterium-mediated transformation techniques have now made the technique applicable to nearly all monocotyledonous plants. For example, Agrobacterium-mediated transformation techniques have now been applied to rice (Hiei et al., 1997; U.S. Pat. No. 5,591,616, specifically incorporated herein by reference in its entirety), wheat (McCormac et al., 1998), barley (Tingay et al., 1997; McCormac et al., 1998), alfalfa (Thomas et al., 1990) and maize (Ishidia et al., 1996).

Modern Agrobacterium transformation vectors are capable of replication in E. coli as well as Agrobacterium, allowing for convenient manipulations as described (Klee et al., 1985). Moreover, recent technological advances in vectors for Agrobacterium-mediated gene transfer have improved the arrangement of genes and restriction sites in the vectors to facilitate the construction of vectors capable of expressing various polypeptide coding genes. The vectors described (Rogers et al., 1987) have convenient multi-linker regions flanked by a promoter and a polyadenylation site for direct expression of inserted polypeptide coding genes and are suitable for present purposes. In addition, Agrobacterium containing both armed and disarmed Ti genes can be used for the transformations. In those plant strains where Agrobacterium-mediated transformation is efficient, it is the method of choice because of the facile and defined nature of the gene transfer.

B. Electroporation

To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wounding in a controlled manner. Examples of some species which have been transformed by electroporation of intact cells include maize (U.S. Pat. No. 5,384,253; Rhodes et al., 1995; D'Halluin et al., 1992), wheat (Zhou et al., 1993), tomato (Hou and Lin, 1996), soybean (Christou et al., 1987) and tobacco (Lee et al., 1989).

One also may employ protoplasts for electroporation transformation of plants (Bates, 1994; Lazzeri, 1995). For example, the generation of transgenic soybean plants by electroporation of cotyledon-derived protoplasts is described by Dhir and Widholm in Intl. Patent Appl. Publ. No. WO 9217598 (specifically incorporated herein by reference). Other examples of species for which protoplast transformation has been described include barley (Lazerri, 1995), sorghum (Battraw et al., 1991), maize (Bhattacharjee et al., 1997), wheat (He et al., 1994) and tomato (Tsukada, 1989).

C. Microprojectile Bombardment

Another method for delivering transforming DNA segments to plant cells in accordance with the invention is microprojectile bombardment (U.S. Pat. No. 5,550,318; U.S. Pat. No. 5,538,880; U.S. Pat. No. 5,610,042; and PCT Application WO 94/09699; each of which is specifically incorporated herein by reference in its entirety). In this method, particles may be coated with nucleic acids and delivered into cells by a propelling force. Exemplary particles include those comprised of tungsten, platinum, and preferably, gold. It is contemplated that in some instances DNA precipitation onto metal particles would not be necessary for DNA delivery to a recipient cell using microprojectile bombardment. However, it is contemplated that particles may contain DNA rather than be coated with DNA. Hence, it is proposed that DNA-coated particles may increase the level of DNA delivery via particle bombardment but are not, in and of themselves, necessary.

For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into plant cells by acceleration is the Biolistics Particle Delivery System, which can be used to propel particles coated with DNA or cells through a screen, such as a stainless steel or Nytex screen, onto a filter surface covered with monocot plant cells cultured in suspension. The screen disperses the particles so that they are not delivered to the recipient cells in large aggregates. Microprojectile bombardment techniques are widely applicable, and may be used to transform virtually any plant species. Examples of species for which have been transformed by microprojectile bombardment include monocot species such as maize (PCT Application WO 95/06128), barley (Ritala et al., 1994; Hensgens et al., 1993), wheat (U.S. Pat. No. 5,563,055, specifically incorporated herein by reference in its entirety), rice (Hensgens et al., 1993), oat (Torbet et al., 1995; Torbet et al., 1998), rye (Hensgens et al., 1993), sugarcane (Bower et al., 1992), and sorghum (Casa et al., 1993; Hagio et al., 1991); as well as a number of dicots including tobacco (Tomes et al., 1990; Buising and Benbow, 1994), soybean (U.S. Pat. No. 5,322,783, specifically incorporated herein by reference in its entirety), sunflower (Knittel et al., 1994), peanut (Singsit et al., 1997), cotton (McCabe and Martinell, 1993), tomato (VanEck et al., 1995), and legumes in general (U.S. Pat. No. 5,563,055, specifically incorporated herein by reference in its entirety).

D. Other Transformation Methods

Transformation of protoplasts can be achieved using methods based on calcium phosphate precipitation, polyethylene glycol treatment, electroporation, and combinations of these treatments (see, e.g., Potrykus et al., 1985; Lorz et al., 1985; Omirulleh et al., 1993; Fromm et al., 1986; Uchimiya et al., 1986; Callis et al., 1987; Marcotte et al., 1988).

Application of these systems to different plant strains depends upon the ability to regenerate that particular plant strain from protoplasts. Illustrative methods for the regeneration of cereals from protoplasts have been described (Toriyama et al., 1986; Yamada et al., 1986; Abdullah et al., 1986; Omirulleh et al., 1993 and U.S. Pat. No. 5,508,184; each specifically incorporated herein by reference in its entirety). Examples of the use of direct uptake transformation of cereal protoplasts include transformation of rice (Ghosh-Biswas et al., 1994), sorghum (Battraw and Hall, 1991), barley (Lazerri, 1995), oat (Zheng and Edwards, 1990) and maize (Omirulleh et al., 1993).

To transform plant strains that cannot be successfully regenerated from protoplasts, other ways to introduce DNA into intact cells or tissues can be utilized. For example, regeneration of cereals from immature embryos or explants can be effected as described (Vasil, 1989). Also, silicon carbide fiber-mediated transformation may be used with or without protoplasting (Kaeppler, 1990; Kaeppler et al., 1992; U.S. Pat. No. 5,563,055, specifically incorporated herein by reference in its entirety). Transformation with this technique is accomplished by agitating silicon carbide fibers together with cells in a DNA solution. DNA passively enters as the cells are punctured. This technique has been used successfully with, for example, the monocot cereals maize (PCT Application WO 95/06128, specifically incorporated herein by reference in its entirety; (Thompson, 1995) and rice (Nagatani, 1997).

E. Tissue Cultures

Tissue cultures may be used in certain transformation techniques for the preparation of cells for transformation and for the regeneration of plants therefrom. Maintenance of tissue cultures requires use of media and controlled environments. "Media" refers to the numerous nutrient mixtures that are used to grow cells in vitro, that is, outside of the intact living organism. The medium usually is a suspension of various categories of ingredients (salts, amino acids, growth regulators, sugars, buffers) that are required for growth of most cell types. However, each specific cell type requires a specific range of ingredient proportions for growth, and an even more specific range of formulas for optimum growth. Rate of cell growth also will vary among cultures initiated with the array of media that permit growth of that cell type.

Nutrient media is prepared as a liquid, but this may be solidified by adding the liquid to materials capable of providing a solid support. Agar is most commonly used for this purpose. Bactoagar, Hazelton agar, Gelrite, and Gelgro are specific types of solid support that are suitable for growth of plant cells in tissue culture.

Some cell types will grow and divide either in liquid suspension or on solid media. As disclosed herein, plant cells will grow in suspension or on solid medium, but regeneration of plants from suspension cultures typically requires transfer from liquid to solid media at some point in development. The type and extent of differentiation of cells in culture will be affected not only by the type of media used and by the environment, for example, pH, but also by whether media is solid or liquid.

Tissue that can be grown in a culture includes meristem cells, Type I, Type II, and Type III callus, immature embryos and gametic cells such as microspores, pollen, sperm and egg cells. Type I, Type II, and Type III callus may be initiated from tissue sources including, but not limited to, immature embryos, seedling apical meristems, root, leaf, microspores and the like. Those cells which are capable of proliferating as callus also are recipient cells for genetic transformation.

Somatic cells are of various types. Embryogenic cells are one example of somatic cells which may be induced to regenerate a plant through embryo formation. Non-embryogenic cells are those which typically will not respond in such a fashion. Certain techniques may be used that enrich recipient cells within a cell population. For example, Type II callus development, followed by manual selection and culture of friable, embryogenic tissue, generally results in an enrichment of cells. Manual selection techniques which can be employed to select target cells may include, e.g., assessing cell morphology and differentiation, or may use various physical or biological means. Cryopreservation also is a possible method of selecting for recipient cells.

Manual selection of recipient cells, e.g., by selecting embryogenic cells from the surface of a Type II callus, is one means that may be used in an attempt to enrich for particular cells prior to culturing (whether cultured on solid media or in suspension).

Where employed, cultured cells may be grown either on solid supports or in the form of liquid suspensions. In either instance, nutrients may be provided to the cells in the form of media, and environmental conditions controlled. There are many types of tissue culture media comprised of various amino acids, salts, sugars, growth regulators and vitamins. Most of the media employed in the practice of the invention will have some similar components, but may differ in the composition and proportions of their ingredients depending on the particular application envisioned. For example, various cell types usually grow in more than one type of media, but will exhibit different growth rates and different morphologies, depending on the growth media. In some media, cells survive but do not divide. Various types of media suitable for culture of plant cells previously have been described. Examples of these media include, but are not limited to, the N6 medium described by Chu et al. (1975) and MS media (Murashige and Skoog, 1962).

Production and Characterization of Stably Transformed Plants

After effecting delivery of exogenous DNA to recipient cells, the next steps generally concern identifying the transformed cells for further culturing and plant regeneration. In order to improve the ability to identify transformants, one may desire to employ a selectable or screenable marker gene with a transformation vector prepared in accordance with the invention. In this case, one would then generally assay the potentially transformed cell population by exposing the cells to a selective agent or agents, or one would screen the cells for the desired marker gene trait.

A. Selection

It is believed that DNA is introduced into only a small percentage of target cells in any one study. In order to provide an efficient system for identification of those cells receiving DNA and integrating it into their genomes one may employ a means for selecting those cells that are stably transformed. One exemplary embodiment of such a method is to introduce into the host cell, a marker gene which confers resistance to some normally inhibitory agent, such as an antibiotic or herbicide. Examples of antibiotics which may be used include the aminoglycoside antibiotics neomycin, kanamycin and paromomycin, or the antibiotic hygromycin. Resistance to the aminoglycoside antibiotics is conferred by aminoglycoside phosphostransferase enzymes such as neomycin phosphotransferase II (NPT II) or NPT I, whereas resistance to hygromycin is conferred by hygromycin phosphotransferase.

Potentially transformed cells then are exposed to the selective agent. In the population of surviving cells will be those cells where, generally, the resistance-conferring gene has been integrated and expressed at sufficient levels to permit cell survival. Cells may be tested further to confirm stable integration of the exogenous DNA.

One herbicide which constitutes a desirable selection agent is the broad spectrum herbicide bialaphos. Bialaphos is a tripeptide antibiotic produced by *Streptomyces hygroscopicus* and is composed of phosphinothricin (PPT), an analogue of L-glutamic acid, and two L-alanine residues. Upon removal of the L-alanine residues by intracellular peptidases, the PPT is released and is a potent inhibitor of glutamine synthetase (GS), a pivotal enzyme involved in ammonia assimilation and nitrogen metabolism (Ogawa et al., 1973). Synthetic PPT, the active ingredient in the herbicide Liberty also is effective as a selection agent. Inhibition of GS in plants by PPT causes the rapid accumulation of ammonia and death of the plant cells.

The organism producing bialaphos and other species of the genus *Streptomyces* also synthesizes an enzyme phosphinothricin acetyl transferase (PAT) which is encoded by the bar gene in *Streptomyces hygroscopicus* and the pat gene in *Streptomyces viridochromogenes*. The use of the herbicide resistance gene encoding phosphinothricin acetyl transferase (PAT) is referred to in DE 3642 829 A, wherein the gene is isolated from *Streptomyces viridochromogenes*. In the bacterial source organism, this enzyme acetylates the free amino group of PPT preventing auto-toxicity (Thompson et al., 1987). The bar gene has been cloned (Murakami et al., 1986; Thompson et al., 1987) and expressed in transgenic tobacco, tomato, potato (De Block et al., 1987) *Brassica* (De Block et al., 1989) and maize (U.S. Pat. No. 5,550,318). In previous reports, some transgenic plants which expressed the resistance gene were completely resistant to commercial formulations of PPT and bialaphos in greenhouses.

Another example of a herbicide which is useful for selection of transformed cell lines in the practice of the invention is the broad spectrum herbicide glyphosate. Glyphosate inhibits the action of the enzyme EPSPS which is active in the aromatic amino acid biosynthetic pathway. Inhibition of this enzyme leads to starvation for the amino acids phenylalanine, tyrosine, and tryptophan and secondary metabolites derived thereof. U.S. Pat. No. 4,535,060 describes the isolation of EPSPS mutations which confer glyphosate resistance on the *Salmonella typhimurium* gene for EPSPS, aroA. The EPSPS gene was cloned from *Zea mays* and mutations similar to those found in a glyphosate resistant aroA gene were introduced in vitro. Mutant genes encoding glyphosate resistant EPSPS enzymes are described in, for example, International Patent WO 97/4103. The best characterized mutant EPSPS gene conferring glyphosate resistance comprises amino acid changes at residues 102 and 106, although it is anticipated that other mutations will also be useful (PCT/WO97/4103).

To use the bar-bialaphos or the EPSPS-glyphosate selective system, transformed tissue is cultured for 0-28 days on nonselective medium and subsequently transferred to medium containing from 1-3 mg/l bialaphos or 1-3 mM glyphosate as appropriate. While ranges of 1-3 mg/l bialaphos or 1-3 mM glyphosate will typically be preferred, it is proposed that ranges of 0.1-50 mg/l bialaphos or 0.1-50 mM glyphosate will find utility.

An example of a screenable marker trait is the enzyme luciferase. In the presence of the substrate luciferin, cells expressing luciferase emit light which can be detected on photographic or x-ray film, in a luminometer (or liquid scintillation counter), by devices that enhance night vision, or by a highly light sensitive video camera, such as a photon counting camera. These assays are nondestructive and transformed cells may be cultured further following identification. The photon counting camera is especially valuable as it allows one to identify specific cells or groups of cells which are expressing luciferase and manipulate those in real time. Another screenable marker which may be used in a similar fashion is the gene coding for green fluorescent protein.

B. Regeneration and Seed Production

Cells that survive the exposure to the selective agent, or cells that have been scored positive in a screening assay, may be cultured in media that supports regeneration of plants. In an exemplary embodiment, MS and N6 media may be modified by including further substances such as growth regulators. One such growth regulator is dicamba or 2,4-D. However, other growth regulators may be employed, including NAA, NAA+2,4-D or picloram. Media improvement in these and like ways has been found to facilitate the growth of cells at specific developmental stages. Tissue may be maintained on a basic media with growth regulators until sufficient tissue is available to begin plant regeneration efforts, or following repeated rounds of manual selection, until the morphology of the tissue is suitable for regeneration, at least 2 wk, then transferred to media conducive to maturation of embryoids. Cultures are transferred every 2 wk on this medium. Shoot development will signal the time to transfer to medium lacking growth regulators.

The transformed cells, identified by selection or screening and cultured in an appropriate medium that supports regeneration, will then be allowed to mature into plants. Developing plantlets are transferred to soilless plant growth mix, and hardened, e.g., in an environmentally controlled chamber, for example, at about 85% relative humidity, 600 ppm $CO_2$, and 25-250 microeinsteins m 2 s−1 of light. Plants may be matured in a growth chamber or greenhouse. Plants can be regenerated from about 6 wk to 10 months after a transformant is identified, depending on the initial tissue. During regeneration, cells are grown on solid media in tissue culture vessels. Illustrative embodiments of such vessels are petri dishes and Plant Cons. Regenerating plants can be grown at about 19 to 28° C. After the regenerating plants have reached the stage of shoot and root development, they may be transferred to a greenhouse for further growth and testing.

Seeds on transformed plants may occasionally require embryo rescue due to cessation of seed development and premature senescence of plants. To rescue developing embryos, they are excised from surface-disinfected seeds 10-20 days post-pollination and cultured. An embodiment of media used for culture at this stage comprises MS salts, 2% sucrose, and 5.5 g/l agarose. In embryo rescue, large embryos (defined as greater than 3 mm in length) are germinated directly on an appropriate media. Embryos smaller than that may be cultured for 1 wk on media containing the above ingredients along with 10-5M abscisic acid and then transferred to growth regulator-free medium for germination.

C. Characterization

To confirm the presence of the exogenous DNA or "transgene(s)" in the regenerating plants, a variety of assays may be performed. Such assays include, for example, "molecular biological" assays, such as Southern and Northern blotting and PCR™; "biochemical" assays, such as detecting the presence of a protein product, e.g., by immunological means (ELISAs and Western blots) or by enzymatic function; plant part assays, such as leaf or root assays; and also, by analyzing the phenotype of the whole regenerated plant.

D. DNA Integration, RNA Expression and Inheritance

Genomic DNA may be isolated from cell lines or any plant parts to determine the presence of the exogenous gene through the use of techniques well known to those skilled in the art. Note, that intact sequences will not always be present, presumably due to rearrangement or deletion of sequences in the cell. The presence of DNA elements introduced through the methods of this invention may be determined, for example, by polymerase chain reaction (PCR™). Using this technique, discreet fragments of DNA are amplified and detected by gel electrophoresis. This type of analysis permits one to determine whether a gene is present in a stable transformant, but does not prove integration of the introduced gene into the host cell genome. It is typically the case, however, that DNA has been integrated into the genome of all transformants that demonstrate the presence of the gene through PCR™ analysis. In addition, it is not typically possible using PCR™ techniques to determine whether transformants have exogenous genes introduced into different sites in the genome, i.e., whether transformants are of independent origin. It is contemplated that using PCR™ techniques it would be possible to clone fragments of the host genomic DNA adjacent to an introduced gene.

Positive proof of DNA integration into the host genome and the independent identities of transformants may be determined using the technique of Southern hybridization. Using this technique specific DNA sequences that were introduced into the host genome and flanking host DNA sequences can be identified. Hence the Southern hybridization pattern of a given transformant serves as an identifying characteristic of that transformant. In addition it is possible through Southern hybridization to demonstrate the presence of introduced genes in high molecular weight DNA, i.e., confirm that the introduced gene has been integrated into the host cell genome. The technique of Southern hybridization provides information that is obtained using PCR™, e.g., the presence of a gene, but also demonstrates integration into the genome and characterizes each individual transformant.

It is contemplated that using the techniques of dot or slot blot hybridization which are modifications of Southern hybridization techniques one could obtain the same information that is derived from PCR™, e.g., the presence of a gene.

Both PCR™ and Southern hybridization techniques can be used to demonstrate transmission of a transgene to progeny. In most instances the characteristic Southern hybridization pattern for a given transformant will segregate in progeny as one or more Mendelian genes (Spencer et al., 1992) indicating stable inheritance of the transgene.

Whereas DNA analysis techniques may be conducted using DNA isolated from any part of a plant, RNA will only be expressed in particular cells or tissue types and hence it will be necessary to prepare RNA for analysis from these tissues. PCR™ techniques also may be used for detection and quantitation of RNA produced from introduced genes. In this application of PCR™ it is first necessary to reverse transcribe RNA into DNA, using enzymes such as reverse transcriptase, and then through the use of conventional PCR™ techniques amplify the DNA. In most instances PCR™ techniques, while useful, will not demonstrate integrity of the RNA product. Further information about the nature of the RNA product may be obtained by Northern blotting. This technique will demonstrate the presence of an RNA species and give information about the integrity of that RNA. The presence or absence of an RNA species also can be determined using dot or slot blot Northern hybridizations. These techniques are modifications of Northern blotting and will only demonstrate the presence or absence of an RNA species.

E. Gene Expression

While Southern blotting and PCR™ may be used to detect the gene(s) in question, they do not provide information as to whether the corresponding protein is being expressed. Expression may be evaluated by specifically identifying the protein products of the introduced genes or evaluating the phenotypic changes brought about by their expression.

Assays for the production and identification of specific proteins may make use of physical-chemical, structural, functional, or other properties of the proteins. Unique physical-chemical or structural properties allow the proteins to be separated and identified by electrophoretic procedures, such as native or denaturing gel electrophoresis or isoelectric focusing, or by chromatographic techniques such as ion exchange or gel exclusion chromatography. The unique structures of individual proteins offer opportunities for use of specific antibodies to detect their presence in formats such as an ELISA assay. Combinations of approaches may be employed with even greater specificity such as western blotting in which antibodies are used to locate individual gene products that have been separated by electrophoretic techniques. Additional techniques may be employed to absolutely confirm the identity of the product of interest such as evaluation by amino acid sequencing following purification. Although these are among the most commonly employed, other procedures may be additionally used.

Assay procedures also may be used to identify the expression of proteins by their functionality, especially the ability of enzymes to catalyze specific chemical reactions involving specific substrates and products. These reactions may be followed by providing and quantifying the loss of substrates or the generation of products of the reactions by physical or chemical procedures. Examples are as varied as the enzyme to be analyzed and may include assays for PAT enzymatic activity by following production of radiolabeled acetylated phosphinothricin from phosphinothricin and 14C-acetyl CoA or for anthranilate synthase activity by following loss of fluorescence of anthranilate, to name two.

Very frequently the expression of a gene product is determined by evaluating the phenotypic results of its expression. These assays also may take many forms including but not limited to analyzing changes in the chemical composition, morphology, or physiological properties of the plant. Chemical composition may be altered by expression of genes encoding enzymes or storage proteins which change amino acid composition and may be detected by amino acid analysis, or by enzymes which change starch quantity which may be analyzed by near infrared reflectance spectrometry. Morphological changes may include greater stature or thicker stalks. Most often changes in response of plants or plant parts to imposed treatments are evaluated under carefully controlled conditions termed bioassays.

Breeding Plants of the Invention

In addition to direct transformation of a particular plant genotype with a construct prepared according to the current invention, transgenic plants may be made by crossing a plant having a selected DNA of the invention to a second plant lacking the construct. For example, a selected lignin biosynthesis coding sequence can be introduced into a particular plant variety by crossing, without the need for ever directly transforming a plant of that given variety. Therefore, the current invention not only encompasses a plant directly transformed or regenerated from cells which have been transformed in accordance with the current invention, but also the progeny of such plants.

As used herein the term "progeny" denotes the offspring of any generation of a parent plant prepared in accordance with the instant invention, wherein the progeny comprises a selected DNA construct. "Crossing" a plant to provide a plant line having one or more added transgenes relative to a starting plant line, as disclosed herein, is defined as the techniques that result in a transgene of the invention being introduced into a plant line by crossing a starting line with a donor plant line that comprises a transgene of the invention. To achieve this one could, for example, perform the following steps:
  (a) plant seeds of the first (starting line) and second (donor plant line that comprises a transgene of the invention) parent plants;
  (b) grow the seeds of the first and second parent plants into plants that bear flowers;
  (c) pollinate a flower from the first parent plant with pollen from the second parent plant; and
  (d) harvest seeds produced on the parent plant bearing the fertilized flower.

Backcrossing is herein defined as the process including the steps of:
  (a) crossing a plant of a first genotype containing a desired gene, DNA sequence or element to a plant of a second genotype lacking the desired gene, DNA sequence or element;
  (b) selecting one or more progeny plant containing the desired gene, DNA sequence or element;
  (c) crossing the progeny plant to a plant of the second genotype; and
  (d) repeating steps (b) and (c) for the purpose of transferring a desired DNA sequence from a plant of a first genotype to a plant of a second genotype.

Introgression of a DNA element into a plant genotype is defined as the result of the process of backcross conversion. A plant genotype into which a DNA sequence has been introgressed may be referred to as a backcross converted genotype, line, inbred, or hybrid. Similarly a plant genotype lacking the desired DNA sequence may be referred to as an unconverted genotype, line, inbred, or hybrid.

EXAMPLES

Example 1: Total PPO Enzyme Activity does not Predict Shelf Life Performance

A panel of 23 cultivars including discoloration controls were sown in a three replicate trial in a single environment. The cultivars were harvested on the same day and total PPO enzymatic activity was determined. A normal distribution of total units of PPO activity (U PPO Activity=uM*min−1*ug−1) was observed amongst the 23 cultivars. The varieties with the five highest and five lowest PPO activities were then grown in a second environment, and shelf life was determined using a 6 replicate randomized complete block design. It was recognized that the harvest activity did not predict shelf life performance, the two most discoloration resistant varieties in this set were identified as having high enzymatic activity. In a comparison of harvest PPO enzymatic activity (total) for 8 different harvests of discoloration controls, 7 of 8 comparisons were not statistically differentiated. These results were surprising and unexpected because Enzymatic activity, the sum total of activity of all active enzymes, had previously been believed to be a predictor of shelf life.

Example 2: PPO11 Expression Increases Over Time after Harvest

Eleven (11) PPO gene homologs, shown in FIG. 1, and 3 PAL gene homologs were identified in lettuce. Gene expression analysis of these discoloration pathway enzyme homologs were evaluated for correlation to discoloration phenotype/shelf life performance. The ability to correlate PPO enzyme activity at harvest or induction of specific pathway genes with shelf life performance provided a focused selection tool to enable a breeding program to improve shelf life performance.

RT PCR protocol: QRT-PCRs were performed as described in the operator's manual using a Stratagene MX3000P™. Gene-specific PCR primers were designed using criteria including predicted melting temperature of at least 58° C., primer length of 22-24 nucleotides, guanosine-cytosine content of at least 48%, and an amplicon length of 120-150 bp. Primer specificity was confirmed by melting curve analysis, by an efficiency of product amplification of 1.0 § 0.1, and by sequence verification of at least eight cloned PCR amplicons for each gene. Reactions with water instead of cDNA template were run with each primer pair as control. The standard thermal profile: 95° C. for 10 min, then 60 cycles of 95° C. for 30 s, 53° C. for 30 s and 72° C. for 30 s was used. The fluorescence signal was captured at the end of each cycle, and a melting curve analysis was performed from the annealing temperature to 95° C. with data capture every 0.2° C. during a 1 s hold. The quantity of each transcript is the average of two technical replicates. All amplification plots were analyzed with the MX3000P™ software to obtain threshold cycle (Ct) values. Transcript abundance was normalized to the transcript abundance of ubiquitin (GenBank accession number EF681766).

Figure 2:
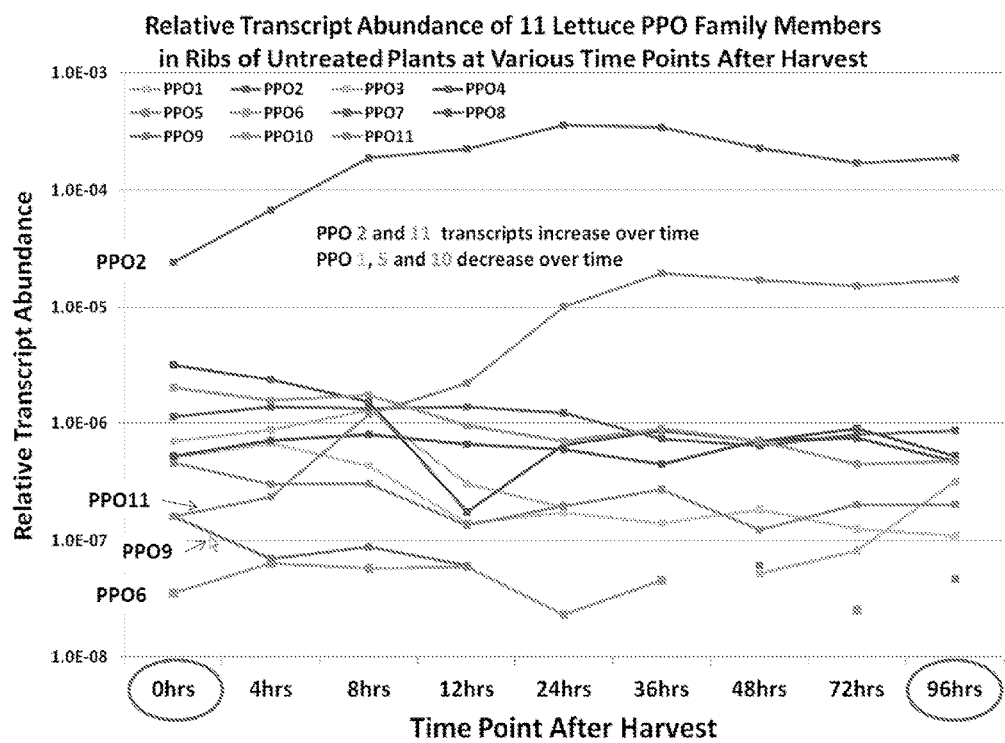
FIG. 2: Transcript abundances of the 11 lettuce PPO genes were assayed at 0, 4, 8, 12, 24, 36, 48, 72, and 96 hours after harvest to identify which PPO genes correlate in expression to the incidence of browning in untreated lettuce ribs. Surprisingly, despite high homology among PPO genes, PPO11 was identified as the transcript whose expression correlated with and predicted the visual browning phenotype.

The results are shown in FIG. 2, which provides a time-course experiment of the expression profile of PPOs. Two homologs of PPO, PPO2 and PPO11, were upregulated after harvest. PPO11 was the most upregulated PPO during the time-course experiment. The expression of PPO1 and PPO10 went down over time. The expression of PPO8 did not change over time.

Example 3: Determining Shelf Life of Lettuce

The current industry standard for assessing lettuce performance, browning, or shelf life is to evaluate a lettuce variety in a modified atmosphere package at 14 days after processing and ensure that less than 2% visible pinking or browning occurs. The performance of individual varieties beyond 4 days has been unknown. The performance of chopped lettuce varieties in an ambient air assay at 4° C. is evaluated. Such evaluation allows lettuce variety performance to be distinguished in a rapid manner. In addition, correlation of polyphenol oxidase enzymatic (PPO) activity in the central rib of each variety with lettuce performance was tested.

To carry out the shelf live evaluation, six heads of lettuce are collected and packaged into a waxed cardboard box. A refrigerated truck, set to 41° F., is used for sample transport.

Individual heads are removed from the plastic bag and the ID tag placed into a single blue tray. Two empty barcoded 50 ml tubes are placed into the tray and the sample can then move on for chopping. Outer damaged leaves are removed and the base is cut off. The stem is removed and discarded, the inner heart leaves (yellow and less than 6 inches long) are discarded. From each head, two leaves from outer and inner leaves are set aside for central rib evaluation, 12 leaves in total are collected. All of the remaining lettuce leaves are chopped for shelf life evaluation.

Central Rib evaluation: From the 12 petioles (6 heads×2 leaves) the upper leafy material and the material from the edge along the bottom ⅔ of the lettuce rib are removed using a knife. The leafy material is discarded and the lower ⅔ of the central ribs are retained. All ribs are chopped into 1 inch slices, mixed by hand and then subsampled into tubes filling to the 30 ml line.

Romaine, CRC, and spinach-type lettuce are prepared as follows. The leafy material above the rib is removed. Excess leafy material parallel to the rib is removed to leave only about 1-2 inches of leafy material on each side of the rib. If the leaf is narrow enough, this step is not performed. The rib and flanking leafy pieces are chopped into ¾ inch pieces perpendicular to the rib length. All material is collected and immersed into cold fresh water using a large screen basket, transferred into an electric salad spinner and dried for 60 seconds. Three amply full quart clamshells (individual barcodes) are collected if available. Any remaining chopped lettuce is collected in a barcoded black tray.

Iceberg type lettuce: are to be prepared as follows: The lettuce is chopped into ¾ inch strips and then these strips are chopped at a 90° angle into ¾ inch squares. All material is collected into a blue bin, washed in mesh basket, and spun dry for 60 seconds in an electric salad spinner. Three amply full quart clamshells (individual barcodes) are collected if available. Any remaining chopped lettuce is collected in a barcoded black tray. The samples are scanned in order, falcon tubes are stored −80° C., and the samples are visually rated and image analysis is performed by Visual Ratings and image analysis.

Visual Ratings: Beginning at 72 hrs after processing, each sample will be scored on a 1 (best) to 5 (worst) rating scale against reference photos by multiple individuals independently. It is necessary to ensure adequate lighting to discern differences in browning. Ideally the samples will be rated at day 3, 5, and 7 according to the reference photos, and the timing of clamshell evaluations to be done as blocks from the field. The combined score for each clamshell will be recorded.

Image Analysis: The lettuce pieces in each black tray will be photographed at the same time points as the visual ratings. A light station with Rosco Litepad HO+, 3"×12" light bars set at a 40° angle from horizontal on either side at a distance of 18" from the work surface will be used. Images are collected with a Canon EOS Rebel T3 that is positioned at 53 cm above the platform. The amount of discoloration is determined by image analysis using a custom Matlab program to quantify the number of brown pixels relative to the number of pixels representing the total lettuce leaf area.

Example 4: Expression of PPO11 Correlates with Browning and Reduced Shelf Life

The levels of expression of PPO2, PPO8, PPO10, PPO11 and PAL1 were determined by testing central mid rib RNA extractions from materials collected at the time of processing or after 7-9 days of storage in ambient air at 4° C. RNA samples were prepared using PureLink® Plant RNA Reagent (Ambion) kit following procedures recommended by the manufacturer. QRT-PCRs were performed as described in the operator's manual using a Stratagene MX3000P™. Gene-specific PCR primers were designed (see Table 2). All amplification plots were analyzed with the MX3000P™ software to obtain threshold cycle (Ct) values. Transcript abundance was normalized to the transcript abundance of ubiquitin (GenBank accession number EF681766).

TABLE 2 Gene-specific PCR primers:

| SEQ ID NOs | Amplicon | Primer Name | Fluorescent Tag | 5'->3' |
|---|---|---|---|---|
| SEQ ID NO: 12 | PAL1 | PAL1-F | — | CGTCGAGATTCTGCGAGAAAG |
| SEQ ID NO: 13 | PAL1 | PAL1-R | — | GCAAACGTCGTCGATGTAAGC |
| SEQ ID NO: 14 | PAL1 | LsPAL1Probe | 6FAM | CTCCTCCGTGTTGTTGATCGTGAATACGTC |
| SEQ ID NO: 15 | PPO1 | PPO1-F | — | GCAAGTTCAATAAAGCCATCGA |
| SEQ ID NO: 16 | PPO1 | PPO1-R | — | CGCAATAGGCACAATGAACATT |
| SEQ ID NO: 17 | PPO1 | LsPPO1Probe | 6FAM | CCCAGATGACGATCCTCGTAGCTTTAAGC |
| SEQ ID NO: 18 | PPO10 | PO10-F | — | AAGGCTTCCAGAAACATCAAGAA |

TABLE 2-continued

Gene-specific PCR primers:

| SEQ ID NOs | Amplicon | Primer Name | Fluorescent Tag | 5'->3' |
|---|---|---|---|---|
| SEQ ID NO: 19 | PPO10 | PPO10-R | — | AGACTCGCCGGAAAAACATCT |
| SEQ ID NO: 20 | PPO10 | LsPPO10Probe | 6FAM | CATGCCCATGAACACATACCCTTTGCA |
| SEQ ID NO: 21 | PPO11 | PPO11-F | — | GCAAGATCAAGAAGCTCGCTGTA |
| SEQ ID NO: 22 | PPO11 | PPO11-R | — | ACTCGCCGGAAAAACATCTTT |
| SEQ ID NO: 23 | PPO11 | LsPPO11Probe | 6FAM | CGAGCCGATGAACACATACCCTTTGC |
| SEQ ID NO: 24 | PPO2 | PPO2-F | — | GACGTACCATGGCTAAAAAGCAA |
| SEQ ID NO: 25 | PPO2 | PPO2-R | — | CGATGGATTTCCTCGCAACT |
| SEQ ID NO: 26 | PPO2 | LsPPO2Probe | 6FAM | CCAGTCCCACGTGCACCCAGG |
| SEQ ID NO: 27 | PPO8 | PPO8-F | — | GCTGCAACAGACCCGGTTA |
| SEQ ID NO: 28 | PPO8 | PPO8-R | — | CTGGCGGGTCCTTCTGATT |
| SEQ ID NO: 29 | PPO8 | LsPPO8Probe | 6FAM | CCGAAGAGGAACAACACAAAGGACTTCCC |
| SEQ ID NO: 30 | Ubiquitin | Ubiquitin-F | — | TTGTCTTGAATTTTAGCTTTGACGTT |
| SEQ ID NO: 31 | Ubiquitin | Ubiquitin-R | — | CCTTGACCGGAAAAACAATCA |
| SEQ ID NO: 32 | Ubiquitin | LsUbiquitinProbe | VIC | TCAATGGTGTCGGAGCTTTCCACTTCC |

Figure 3A:
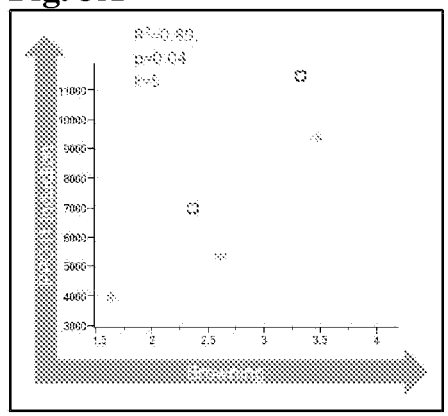
FIGS. 3A-B.
Figure 4:
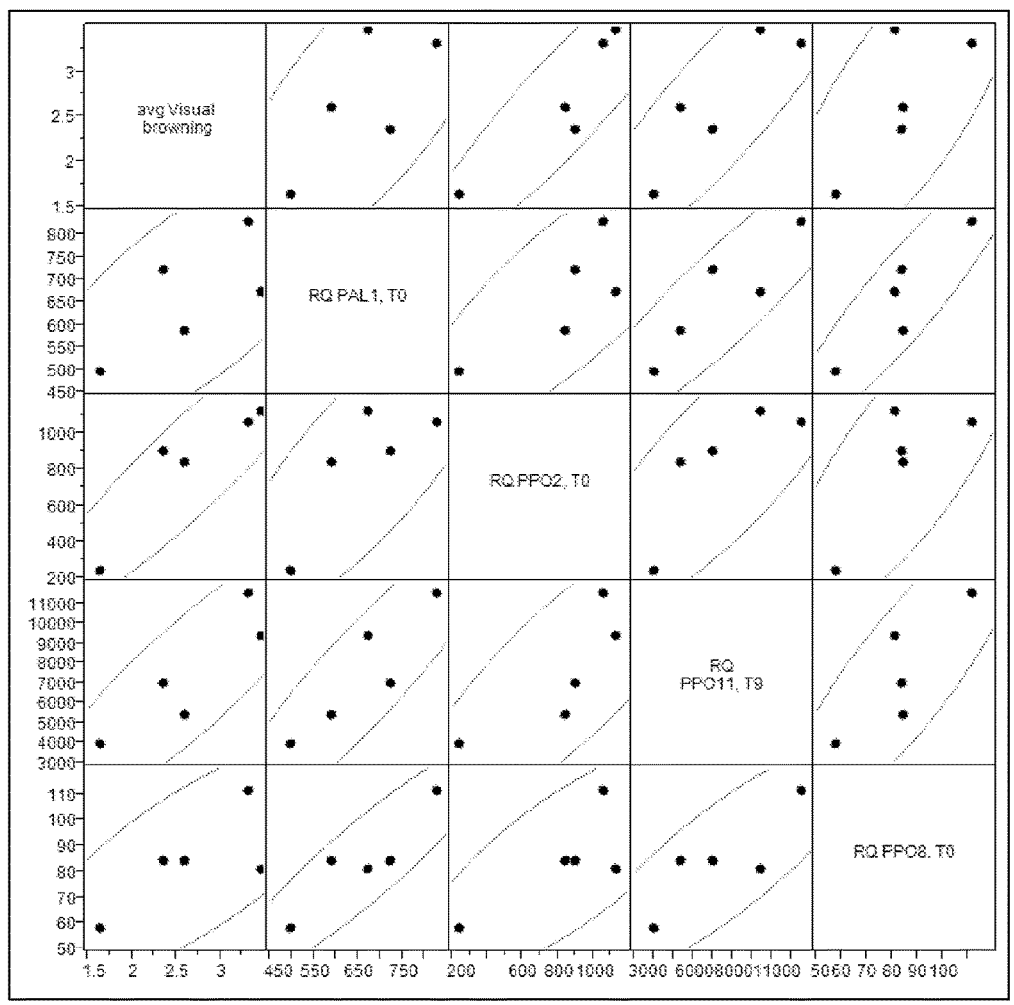
FIG. 4: Plot of Visual Discoloration vs PAL1, $T_0$; vs PPO2, $T_0$; vs PPO11, $T_9$; vs PPO8, $T_0$. RQ PAL 1, $T_0$=relative quantification to ubiquitin (RQ) for phenylalanine lyase homolog 1 (PAL1), at time 0 ($T_0$). This correlation matrix produced in JMPv10 shows the individual variable, i.e. average visual browning scores on the vertical axis in the row the variable is listed and on the horizontal axis in the column it is listed. Plotted are the most correlated gene expression at harvest or 9 days after processing. PPO11 shows the largest range of expression (~200 to ~11000).
Figure 5:
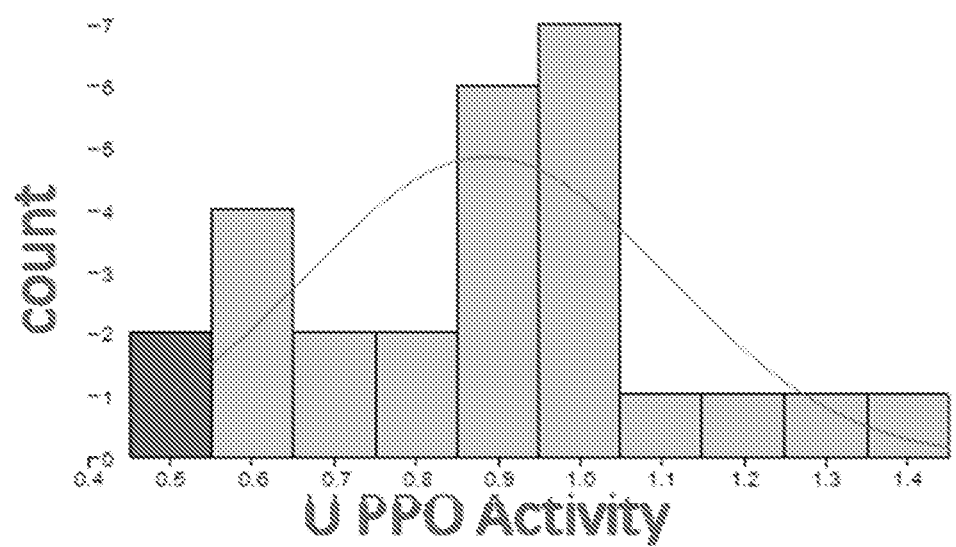
FIG. 5: Depicted is a histogram of total PPO activity (uM*min−1*ug−1 conversion of catechol) for a population of 23 Romaine cultivars as assessed from central midrib tissue at time of processing. Counts on the vertical axis are the number of cultivars with a U PPO activity in the indicated range. This shows from a selection of elite Romaine cultivars that there is 3-fold range in total PPO activity in the central midrib tissue. Sub-selections of the highest and lowest PPO activity cultivars from this experiment were chosen to phenotype for visual discoloration/ shelf life.
Figure 6:
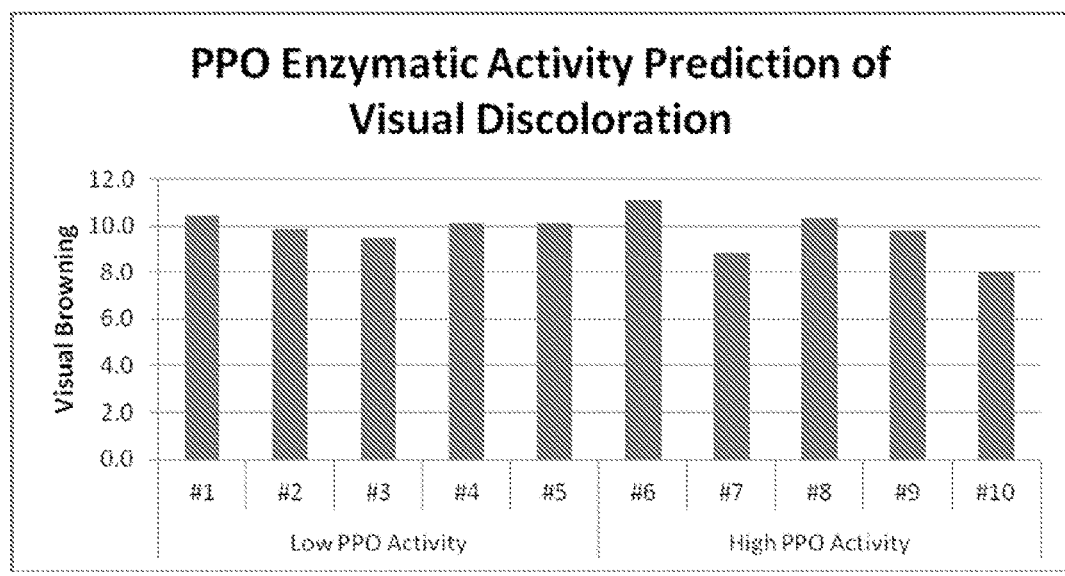
FIG. 6: PPO Enzymatic Activity Predictions of visual Discoloration. Depicted is a bar chart of the visual discoloration for a subset of lines previously selected to have the highest or lowest U PPO activity from a selection of 23 Romaine as described (see FIG. 5). Larger numbers on the vertical axis indicated more discoloration. The coded cultivars are grouped by previously determined high or low PPO activity. The activity level was not predictive of shelf life, as two of the highest enzymatic activity lines were the most resistant in discoloration phenotype.

A plot of Visual Discoloration vs the gene×time point combinations with an r>0.7 are shown in FIG. 3a and FIG. 4. PPO11 was weakly expressed or not expressed at harvest time but was strongly induced after processing and storage. PPO11 induction was observed to have the largest range of range of expression, as demonstrated in FIG. 5.

Figure 3B:
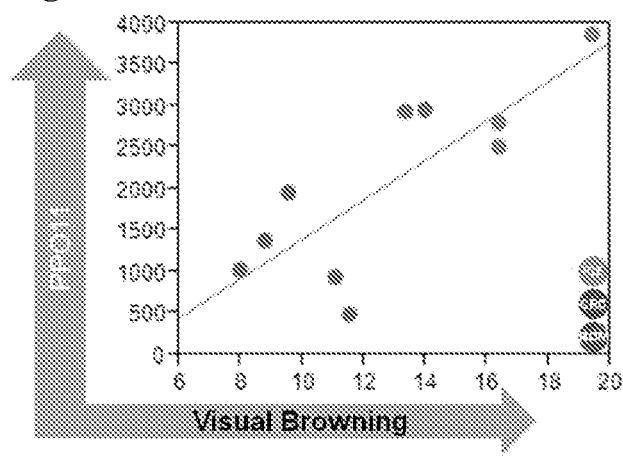

The correlation of PPO11 expression and visual discoloration in a large scale experiment in a different environment is shown in FIG. 3B. Again, the PPO11 expression levels 9 days after processing and cold storage with visual discoloration ratings for two crisphead romaine cross, three iceberg, and five Romaine cultivars was significant. Each point represents the least square mean for a single cultivar with six biological replicates for both gene expression and visual ratings.

In sum, the correlation of expression of PPO11 with a visual browning phenotype was demonstrated in FIGS. 3A-B, and a plot of visual discoloration was provided in FIG. 4, demonstrating that browning was strongly correlated with expression of PPO11.

Example 5: Marker Selection May be Used to Track the PPO11 Locus

Genetic marker sequences associated with a PPO11 locus with reduced gene expression may be used to track that locus in a breeding program. A PPO11 gene or ortholog thereof gene with reduced expression may be identified, for example, by screening for naturally occurring low expressing lines or by one of the methodologies outlined herein. Once a reduced expression PPO11 locus is identified or made, marker sequences associated with the PPO11 locus may be used to track the reduced expression locus in segregating progeny from a plant cross. For example, sequence may be PCR-amplified from sequences flanking PPO11, such as SEQ ID NO:10 and SEQ ID NO:11 and across the PPO11 genetic region in both parents of the cross. Single nucleotide polymorphisms or sequence differences between the two parents may be compared to identify specific alleles from each parent associated with the normal expression or reduced expression PPO11 gene. Sequence-based assay, (e.g. TaqMan) of these single nucleotide polymorphisms or sequence differences in the segregating progeny of a cross will allow selection of the marker allele linked to the desirable reduced expression PPO11 gene.

Example 6: Identification of PPO Targets in Potato and Apple

The PPO11 sequence included here may be used to search potato and apple genome sequence data for PPO homologs.

Using the methods detailed here, expression data from these PPO genes can be correlated with the incidence of browning to identify PPO homolog targets for increasing shelf life. Once appropriate targets are identified, their reduced expression may be identified or brought about and tracked via the methodologies described here.

What is claimed is:

1. A method for identifying plants having reduced expression or lacking expression of a PPO11 gene, comprising:
   a) obtaining a plurality of plants;
   b) screening the plurality of plants for expression of a PPO11 gene having at least 95% sequence identity to SEQ ID NO:9 in which expression is positively correlated with browning or reduced shelf life of a processed product of the plant;
   c) selecting one or more screened plants comprising decreased expression of the PPO11 gene relative to expression of the PPO11 gene in a reference plant of the same crop species, a parent plant, or an otherwise isogenic plant, and which displays browning or reduced shelf life.

2. The method of claim 1, wherein the plurality of plants are obtained by random mutagenesis to obtain plants having reduced expression or lacking expression of the PPO11 gene.

3. The method of claim 1, wherein the plurality of plants are transgenic plants.

4. The method of claim 1, wherein the plurality of plants comprise 10, 100, or 1000 or more plants.

5. The method of claim 1, wherein the plurality of plants are varieties of the same species of plants.

6. The method of claim 1, wherein screening for expression of the PPO11 gene comprises determining an abundance of PPO11 RNA, determining PPO11 activity, or determining abundance of a protein or RNA encoded by SEQ ID NO:9.

7. The method of claim 1, further comprising crossing the one or more plants with reduced expression of PPO11 to a different plant.

8. A method of lettuce breeding comprising:
   a) identifying a first lettuce plant according to the method of claim 1; and
   b) crossing the first lettuce plant with itself or a second lettuce plant to produce progeny lettuce plants having reduced expression or lacking expression of the PPO11 gene.

9. The method of claim 1, wherein said plants are lettuce plants.

* * * * *